US012741015B2

(12) United States Patent
Ichim et al.

(10) Patent No.: US 12,741,015 B2
(45) Date of Patent: Sep. 22, 2026

(54) SUPPRESSION OF DIABETES USING EXOSOMES FROM STEM CELL PROGRAMMED MYELOID CELLS

(71) Applicant: CREATIVE MEDICAL TECHNOLOGIES INC., Phoenix, AZ (US)

(72) Inventors: Thomas Ichim, San Diego, CA (US); Amit Patel, Salt Lake City, UT (US)

(73) Assignee: Creative Medical Technologies, Phoenix, AZ (US)

( * ) Notice: Subject to any disclaimer, the term of this patent is extended or adjusted under 35 U.S.C. 154(b) by 955 days.

(21) Appl. No.: 17/931,868

(22) Filed: Sep. 13, 2022

(65) Prior Publication Data

US 2023/0302105 A1 Sep. 28, 2023

Related U.S. Application Data

(60) Provisional application No. 63/248,324, filed on Sep. 24, 2021.

(51) Int. Cl.

*A61K 8/14* (2006.01)
*A61K 35/28* (2015.01)
*A61K 39/00* (2006.01)
*C12N 5/0775* (2010.01)
*C12N 5/078* (2010.01)

(52) U.S. Cl.

CPC ............ *A61K 39/0008* (2013.01); *A61K 8/14* (2013.01); *A61K 35/28* (2013.01); *C12N 5/0634* (2013.01); *C12N 5/0665* (2013.01); *A61K 2039/5158* (2013.01); *A61K 2039/55555* (2013.01); *A61K 2039/577* (2013.01); *C12N 2502/1352* (2013.01); *C12N 2502/137* (2013.01)

(58) Field of Classification Search

CPC ............ C12N 5/0665; C12N 2502/137; C12N 5/0634; C12N 2502/1352; A61K 8/14; A61K 2039/55555; A61K 39/0005; A61K 39/0008; A61K 35/28; A61K 2039/5158

See application file for complete search history.

(56) References Cited

PUBLICATIONS

Bagno et al. Mechanism of Action of Mesenchymal Stem Cells (MSCs): impact of delivery method. Exp Opin Biol Ther 22(4): 449-463, 2022.*

Cianciaruso et al. Primary Human and Rat B-Cells Release the Intracellular Autoantigens GAD65, IA-2, and Proinsulin in Exosomes Together With Cytokine-Induced Enhancers of Immunity. Diabetes 66: 460-473, 2017.*

DiMeglio et al. Type 1 diabetes. Lancet 391: 2449-2462, 2018.*

Dini et al. Microvesicles and exosomes in metabolic diseases and inflammation. Cytokine Growth Factor Rev 51: 27-39, 2020.*

Favaro et al. Human mesenchymal stem cells and derived extracellular vesicles induce regulatory dendritic cells in type 1 diabetic patients. Diabetologia 59: 325-333, 2016.*

Hasilo et al. Presence of diabetes autoantigens in extracellular vesicles derived from human islets. Sci Reports 7: 5000, 2017 (14 total pages).*

Lu et al. The Role of Extracellular Vesicles in the Pathogenesis and Treatment of Autoimmune Disorders. Front Immunol 12: 566299, 2021 (12 total pages).*

Ma et al. Immunobiology of mesenchymal stem cells. Cell Death Different 21: 216-225, 2014.*

Mahalingaiah et al. An In Vitro Model of Hematotoxicity: Differentiation of Bone Marrow-Derived Stem/Progenitor Cells into Hematopoietic Lineages and Evaluation of Lineage-Specific Hematotoxicity. Current Protocol Toxicol e45, doi: 10.1002/cptx.45, 2018 (21 total pages).*

Marin-Gallen et al. Dendritic cells pulsed with antigen-specific apoptotic bodies prevent experimental type 1 diabetes. Clin Exp Immunol 160: 207-214, 2009.*

Purcell et al. The Evolving Landscape of Autoantigen Discovery and Characterization in Type 1 Diabetes. Diabetes 58: 879-886, 2019.*

Zhang et al. Immunotherapeutic potential of extracellular vesicles. Front Immunol 5: 518, 2014 (11 total pages).*

Zhang et al. Antigen-specific immunotherapies in type 1 diabetes. J Trace Elem Med Biol 73: 127040, 2022 (11 total pages).*

* cited by examiner

*Primary Examiner* — Bridget E Bunner

(74) *Attorney, Agent, or Firm* — Baumgartner Patent Law, LLC; Marc Baumgartner

(57) ABSTRACT

Described are antigen specific and antigen non-specific means of suppressing development of Type 1 Diabetes in a mammal through administration of exosomes, microvesicles or apoptotic bodies from monocytic lineage cells that have been reprogrammed by contact with mesenchymal stem cells and/or mesenchymal stem cell conditioned media. In one embodiment, the invention provides administration of exosomes that have been generated from monocytic cells that have been loaded with tolerogenic antigens and/or epitopes. In another embodiment the invention provides administration of allogeneic myeloid derived exosomes that are loaded with tolerogenic antigens. In another embodiment the invention provides means of stimulating exosome release in vivo from allogeneic cells that have been administered to the patient in need of treatment.

8 Claims, No Drawings

Specification includes a Sequence Listing.

SEQUENCE LISTING

```
Sequence total quantity: 22
SEQ ID NO: 1            moltype = AA  length = 39
FEATURE                 Location/Qualifiers
source                  1..39
                        mol_type = protein
                        organism = Heloderma suspectum
SITE                    39
                        note = Amidated residue
SEQUENCE: 1
HGEGTFTSDL SKQMEEEAVR LFIEWLKNGG PSSGAPPPS                        39

SEQ ID NO: 2            moltype = AA  length = 39
FEATURE                 Location/Qualifiers
source                  1..39
                        mol_type = protein
                        organism = Heloderma horridum
SITE                    39
                        note = Amidated residue
SEQUENCE: 2
HSDGTFTSDL SKQMEEEAVR LFIEWLKNGG PSSGAPPPS                        39

SEQ ID NO: 3            moltype = AA  length = 39
FEATURE                 Location/Qualifiers
source                  1..39
                        mol_type = protein
```

```
                        organism = synthetic construct
SITE                    39
                        note = Amidated residue
SEQUENCE: 3
HGEGTFTSDL SKQLEEEAVR LFIEWLKNGG PSSGAPPPS                        39

SEQ ID NO: 4            moltype = AA  length = 39
FEATURE                 Location/Qualifiers
source                  1..39
                        mol_type = protein
                        organism = synthetic construct
SITE                    39
                        note = Amidated residue
SEQUENCE: 4
HGEGTFTSDL SKQLEEEAVR LFIEFLKNGG PSSGAPPPS                        39

SEQ ID NO: 5            moltype = AA  length = 39
FEATURE                 Location/Qualifiers
source                  1..39
                        mol_type = protein
                        organism = synthetic construct
SITE                    39
                        note = Amidated residue
SEQUENCE: 5
HGEGTFTSDL SKQLEEEAAR LFIEFLKNGG PSSGAPPPS                        39

SEQ ID NO: 6            moltype = AA  length = 30
FEATURE                 Location/Qualifiers
source                  1..30
                        mol_type = protein
                        organism = synthetic construct
SEQUENCE: 6
HGEGTFTSDL SKQMEEEAVR LFIEWLKNGG                                  30

SEQ ID NO: 7            moltype = AA  length = 30
FEATURE                 Location/Qualifiers
source                  1..30
                        mol_type = protein
                        organism = synthetic construct
SEQUENCE: 7
HGEGTFTSDL SKQLEEEAVR LFIEWLKNGG                                  30

SEQ ID NO: 8            moltype = AA  length = 30
FEATURE                 Location/Qualifiers
source                  1..30
                        mol_type = protein
                        organism = synthetic construct
SEQUENCE: 8
HGEGTFTSDL SKQLEEEAVR LFIEFLKNGG                                  30

SEQ ID NO: 9            moltype = AA  length = 30
FEATURE                 Location/Qualifiers
source                  1..30
                        mol_type = protein
                        organism = synthetic construct
SEQUENCE: 9
HGEGTFTSDL SKQLEEEAAR LFIEFLKNGG                                  30

SEQ ID NO: 10           moltype = AA  length = 28
FEATURE                 Location/Qualifiers
source                  1..28
                        mol_type = protein
                        organism = synthetic construct
SEQUENCE: 10
HGEGTFTSDL SKQMEEEAVR LFIEWLKN                                    28

SEQ ID NO: 11           moltype = AA  length = 28
FEATURE                 Location/Qualifiers
source                  1..28
                        mol_type = protein
                        organism = synthetic construct
SEQUENCE: 11
HGEGTFTSDL SKQLEEEAVR LFIEWLKN                                    28

SEQ ID NO: 12           moltype = AA  length = 28
FEATURE                 Location/Qualifiers
source                  1..28
                        mol_type = protein
                        organism = synthetic construct
```

```
SEQUENCE: 12
HGEGTFTSDL SKQLEEEAVR LFIEFLKN                                      28

SEQ ID NO: 13           moltype = AA  length = 28
FEATURE                 Location/Qualifiers
source                  1..28
                        mol_type = protein
                        organism = synthetic construct
SEQUENCE: 13
HGEGTFTSDL SKQLEEEAAR LFIEFLKN                                      28

SEQ ID NO: 14           moltype = AA  length = 39
FEATURE                 Location/Qualifiers
source                  1..39
                        mol_type = protein
                        organism = synthetic construct
SITE                    39
                        note = Amidated residue
SEQUENCE: 14
HGEGTFTSDL SKQLEEKAAK EFIEFLKQGG PSSGAPPPS                          39

SEQ ID NO: 15           moltype = AA  length = 39
FEATURE                 Location/Qualifiers
source                  1..39
                        mol_type = protein
                        organism = synthetic construct
SITE                    39
                        note = Amidated residue
SEQUENCE: 15
HGEGTFTSDL SKQLEEKAAK EFIEWLKQGG PSSGAPPPS                          39

SEQ ID NO: 16           moltype = AA  length = 46
FEATURE                 Location/Qualifiers
source                  1..46
                        mol_type = protein
                        organism = synthetic construct
SITE                    39
                        note = Amidated residue
SEQUENCE: 16
HGEGGGGGGG GTFTSDLSKQ MEEEAVRLFI EWLKQGGPSS GAPPPS                  46

SEQ ID NO: 17           moltype = AA  length = 46
FEATURE                 Location/Qualifiers
source                  1..46
                        mol_type = protein
                        organism = synthetic construct
SITE                    39
                        note = Amidated residue
SEQUENCE: 17
HGEGTFTSDL SKQLEEEAVR LFIEWLKQGG PSSGGGGGGG GAPPPS                  46

SEQ ID NO: 18           moltype = AA  length = 37
FEATURE                 Location/Qualifiers
source                  1..37
                        mol_type = protein
                        organism = synthetic construct
SEQUENCE: 18
HGEFTFTSDL SKQLEEEAVR LFIEWLKQGG PSKEIIS                            37

SEQ ID NO: 19           moltype = AA  length = 39
FEATURE                 Location/Qualifiers
source                  1..39
                        mol_type = protein
                        organism = synthetic construct
SITE                    39
                        note = Amidated residue
SEQUENCE: 19
HGEFTFTSDL SKQLEEKAAK EFIEWLKQGG PSSGAPPPS                          39

SEQ ID NO: 20           moltype = AA  length = 39
FEATURE                 Location/Qualifiers
source                  1..39
                        mol_type = protein
                        organism = synthetic construct
SITE                    39
                        note = Amidated residue
SEQUENCE: 20
HGEGTFTSDL VKILEAEAVR KFIEFLKNGG PSSGAPPPS                          39
```

-continued

```
SEQ ID NO: 21          moltype = AA  length = 40
FEATURE                Location/Qualifiers
source                 1..40
                       mol_type = protein
                       organism = synthetic construct
SEQUENCE: 21
HGEGTFTSDL SKQMEEEAVR LFIEWLKNGG PSSGAPPPSK                  40

SEQ ID NO: 22          moltype = AA  length = 31
FEATURE                Location/Qualifiers
source                 1..31
                       mol_type = protein
                       organism = unidentified
SEQUENCE: 22
HAEGTFTSDV SSYLEGQAAK EFIAWLVKGR G                           31
```

SUPPRESSION OF DIABETES USING EXOSOMES FROM STEM CELL PROGRAMMED MYELOID CELLS

CROSS-REFERENCE TO RELATED APPLICATIONS

This application is a non-provisional of and claims priority to U.S. Provisional Application Ser. No. 63/248,324, filed Sep. 24, 2021, which is hereby incorporated by reference in its entirety.

SEQUENCE LISTING

The instant application contains a Sequence Listing which has been submitted electronically in XML format and is hereby incorporated by reference in its entirety. Said XML copy, created on Jun. 2, 2023, is named CMT_DiaMyeExo_NP1_SL.xml and is 24,757 bytes in size.

FIELD OF THE INVENTION

The invention belongs to the field of diabetes therapy, more specifically the invention belongs to the field of controlling and/or reversing autoimmune diabetes by immune modulation, more specifically, the invention provides means of stimulation of anergy and/or tolerogenesis through administration of microvesicles that either antigen specifically or antigen non-specifically inhibit anti-islet immunity.

BACKGROUND

The development of dysglycemia in type 1 diabetes represents the end stage of a period of silent, immune-mediated beta cell decay [1-7]. Around the time of diagnosis it is estimated that up to 90% of functional beta cell mass is destroyed, although most patients still produce variable amounts of insulin as measured by C-peptide secretion [8-13]. The natural course of T1D prior to diagnosis remains elusive, but relatively accurate risk predictions can be performed based on genetic screening and detection of islet autoantibodies [14-18]. It is well established that effector mechanisms in T1D are primarily T cell-driven, as attested to by the predominance of T cells in the characteristic islet infiltrate after diagnosis and the ability of certain T cell clones to directly kill beta cells [19-27]. Additionally, myeloid cells such as macrophages have also been shown to play a role in beta cell destruction [28].

Replenishing the functional beta cell pool by transplantation or regeneration of insulin-producing cells, although temporarily successful, does not offer a longstanding cure without prevention [29-39], since these cells will be recognized and attacked by persisting autoreactive memory T cells. The invention provides novel means of inducing immune modulation so as to suppress immune responses against pancreatic islets. Suppression of such immune responses has previously been performed utilizing approaches that globally inhibit immunity. Unfortunately, such approaches are often associated with toxicities. For example, there were studies in which the immune suppressive agent cyclosporine was given to type 1 diabetes. Cyclosporin is a calcineurin inhibitor which has been used in the context of transplantation to prevent rejection [40]. In a clinical trial, 122 patients aged 15-40 years with insulin-dependent diabetes of recent onset were randomly assigned to cyclosporin 7.5 mg/kg per day or placebo. At the sixth month 25.4% of the cyclosporin group and 18.6% of the placebo group were in complete remission (not a significant difference). Treatment was continued in those patients with complete or partial remission (insulin requirement less than 0.25 U/kg per day) and 106 patients were followed to nine months, at which stage 24.1% of the original cyclosporin group and 5.8% of the original placebo group were in complete remission (p less than 0.01). For those patients whose whole-blood trough cyclosporin levels in the first three months averaged 300 ng/ml or more, the rates of complete remission at six and nine months were 37.5% and 37%. The rates of partial remission were also higher in the cyclosporin group and at six months the rate of complete or partial remission was 46% in the whole cyclosporin group and 65.6% in those with an average blood level exceeding 300 ng/ml in the first three months, versus 28.8% in the placebo group. The principal side-effect of cyclosporin was a modest and reversible increase in plasma creatinine [41]. Other studies have demonstrated some effect of this agent [42-82].

Another immune suppressant, azathioprine, demonstrated some clinical signal of efficacy. In one study, azathioprine (2 mg/kg) was given, in addition to routine insulin treatment, to alternate patients presenting with recent-onset type I diabetes. Treated (N=13) and untreated (N=11) patients did not differ significantly at diagnosis with respect to age, duration of symptoms, body weight, blood glucose, hemoglobin A1c, or presence of ketosis. Eight patients were treated for 12 mo, three elected to stop treatment at 6 mo, and treatment was stopped in two because of side effects. Seven treated patients had a remission compared with one untreated patient. At 12 mo these seven patients were distinguished by significantly higher basal and glucagon-stimulated levels of C-peptide (1.98+/−0.52 and 3.88+/−0.34 micrograms/L, respectively) compared with the other six treated patients (0.93+/−0.52 and 1.32+/−0.85 microgram/L, respectively), and by the persistence of islet cell cytoplasmic antibodies. Remissions were not sustained in the 1-2 yr after treatment, although relapsed patients required less insulin for control [83]. Other studies have attempted other non-specific immune suppressive agents such as FK-506 [84-86], rapamycin [87-90] with little overall success.

SUMMARY

Embodiments herein are directed to methods of preventing or treating type 1 diabetes comprising the steps of: a) identifying a patient suffering from type 1 diabetes or at risk of type 1 diabetes; b) withdrawing from said patient a population of myeloid lineage cells; c) contacting said myeloid lineage cells with a mesenchymal stem cell population and/or products generated from said mesenchymal stem cell population; d) optionally pulsing said myeloid cell population with one or more antigens associated with diabetes; e) extracting microvesicles from said myeloid cell population; and f) administering said microvesicles from said myeloid cell population into a patient in need of prophylaxis or treatment.

Preferred methods include embodiments wherein said risk of type 1 diabetes is quantified by one or more selected from a group comprising of: a) increase production of interferon gamma from T cells responding to a diabetogenic antigen as compared to T cells from an age-matched subject; b) decreased production of interleukin-4 from T cells responding to a diabetogenic antigen as compared to T cells from an age-matched subject; c) increased antibodies to a diabetogenic antigen as compared to T cells from an age-matched subject.

Preferred methods include embodiments wherein said T cells are selected from a group of T cells comprising of: a) CD3 T cells; b) CD4 T cells; c) CD8 T cells; d) Th1 T cells; e) Th2; f) Th3 T cells; g) Th9 T cells; h) Th17 T cells and i) Th22 T cells.

Preferred methods include embodiments wherein said antibody is a complement fixing antibody.

Preferred methods include embodiments wherein said antibody possesses the isotype IgG2b.

Preferred methods include embodiments wherein said myeloid cell population comprises monocytes.

Preferred methods include embodiments wherein said myeloid cell population comprises monocytic progenitors.

Preferred methods include embodiments wherein said myeloid cell population comprises macrophages.

Preferred methods include embodiments wherein said myeloid cell population comprises dendritic cells.

Preferred methods include embodiments wherein said myeloid cell population comprises dendritic cell progenitors.

Preferred methods include embodiments wherein said myeloid cell population comprises myeloid suppressor cells.

Preferred methods include embodiments wherein said myeloid cell population comprises myeloid suppressor cell progenitors.

Preferred methods include embodiments wherein said mesenchymal stem cells are derived from fluids.

Preferred methods include embodiments wherein said fluid is plasma.

Preferred methods include embodiments wherein said fluid is cerebral spinal fluid.

Preferred methods include embodiments wherein said fluid is urine.

Preferred methods include embodiments wherein said fluid is seminal fluid.

Preferred methods include embodiments wherein said mesenchymal stem cells are derived from tissues.

Preferred methods include embodiments wherein said tissue derived mesenchymal stem cells are selected from a group comprising of: a) bone marrow; b) perivascular tissue; c) adipose tissue; d) placental tissue; e) amniotic membrane; f) omentum; g) tooth; h) umbilical cord tissue; i) fallopian tube tissue; j) hepatic tissue; k) renal tissue; l) cardiac tissue; m) tonsillar tissue; n) testicular tissue; o) ovarian tissue; p) neuronal tissue; q) auricular tissue; r) colonic tissue; s) submucosal tissue; t) hair follicle tissue; u) pancreatic tissue; v) skeletal muscle tissue; and w) subepithelial umbilical cord tissue.

Preferred methods include embodiments wherein said tissue derived mesenchymal stem cells are isolated from tissues containing cells selected from a group of cells comprising of: endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

Preferred methods include embodiments wherein said mesenchymal stem cells are plastic adherent.

Preferred methods include embodiments wherein said mesenchymal stem cells express a marker selected from a group comprising of: a) CD73; b) CD90; and c) CD105.

Preferred methods include embodiments wherein said mesenchymal stem cells are derived from umbilical cord tissue and lack expression of a marker selected from a group comprising of: a) CD14; b) CD45; and c) CD34.

Preferred methods include embodiments wherein said mesenchymal stem cells from umbilical cord tissue express markers selected from a group comprising of; a) oxidized low density lipoprotein receptor 1, b) chemokine receptor ligand 3; and c) granulocyte chemotactic protein.

Preferred methods include embodiments wherein said mesenchymal stem cells from umbilical cord tissue do not express markers selected from a group comprising of: a) CD117; b) CD31; c) CD34; and CD45;

Preferred methods include embodiments wherein said mesenchymal stem cells from umbilical cord tissue express, relative to a human fibroblast, increased levels of interleukin 8 and reticulon 1

Preferred methods include embodiments wherein said mesenchymal stem cells from umbilical cord tissue have the potential to differentiate into cells of at least a skeletal muscle, vascular smooth muscle, pericyte or vascular endothelium phenotype.

Preferred methods include embodiments wherein said mesenchymal stem cells from umbilical cord tissue express markers selected from a group comprising of: a) CD10; b) CD13; c) CD44; d) CD73; and e) CD90.

Preferred methods include embodiments wherein said umbilical cord tissue mesenchymal stem cell is an isolated umbilical cord tissue cell isolated from umbilical cord tissue substantially free of blood that is capable of self-renewal and expansion in culture, Preferred methods include embodiments wherein said umbilical cord tissue mesenchymal stem cells has the potential to differentiate into cells of other phenotypes.

Preferred methods include embodiments wherein said other phenotypes comprise: a) osteocytic; b) adipogenic; and c) chondrogenic differentiation.

Preferred methods include embodiments wherein said cord tissue derived mesenchymal stem cells can undergo at least 20 doublings in culture.

Preferred methods include embodiments wherein said cord tissue derived mesenchymal stem cell maintains a normal karyotype upon passaging Preferred methods include embodiments wherein said cord tissue derived mesenchymal stem cell expresses a marker selected from a group of markers comprised of: a) CD10 b) CD13; c) CD44; d) CD73; e) CD90; f) PDGFr-alpha; g) PD-L2; and h) HLA-A,B,C Preferred methods include embodiments wherein said cord tissue mesenchymal stem cells does not express one or more markers selected from a group comprising of; a) CD31; b) CD34; c) CD45; d) CD80; e) CD86; f) CD117; g) CD141; h) CD178; i) B7-H2; j) HLA-G and k) HLA-DR, DP,DQ.

Preferred methods include embodiments wherein said umbilical cord tissue-derived cell secretes factors selected from a group comprising of: a) MCP-1; b) MIP1beta; c) IL-6; d) IL-8; e) GCP-2; f) HGF; g) KGF; h) FGF; i) HB-EGF; j) BDNF; k) TPO; l) RANTES; and m) TIMP1

Preferred methods include embodiments wherein said umbilical cord tissue derived cells express markers selected from a group comprising of: a) TRA1-60; b) TRA1-81; c) SSEA3; d) SSEA4; and e) NANOG.

Preferred methods include embodiments wherein said umbilical cord tissue-derived cells are positive for alkaline phosphatase staining.

Preferred methods include embodiments wherein said microvesicles are exosomes.

Preferred methods include embodiments wherein said microvescicles are apoptotic bodies.

DETAILED DESCRIPTION OF THE INVENTION

The invention provides means of preventing and/or reversing autoimmune diabetes through administration of microvesicles derived from myeloid cells that have been programmed with regenerative cells such as mesenchymal stem cells. Reprogramming includes direct contact and/or culture with conditioned media of myeloid derived cells from the patient with said regenerative cells.

In one embodiment of the invention regeneration of pancreatic tissue is induced by administration of autologous peripheral blood mononuclear cells that have been cultured with regenerative cells. In one embodiment said regenerative cells are umbilical cord mesenchymal stem cells. In one embodiment cells are cultured at a ratio of 1 peripheral blood mononuclear cell to one umbilical cord mesenchymal stem cell. In one embodiment cells are Throughout this specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the disclosure may "consist essentially of" or "consist of" one or more sequences of the invention, for example. Some embodiments may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

Throughout this specification, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "administered" or "administering", as used herein, refers to any method of providing a composition to an individual such that the composition has its intended effect on the patient. For example, one method of administering is by an indirect mechanism using a medical device such as, but not limited to a catheter, applicator gun, syringe, etc. A second exemplary method of administering is by a direct mechanism such as, local tissue administration, oral ingestion, transdermal patch, topical, inhalation, suppository, etc.

The term "allogeneic," as used herein, refers to cells of the same species that differ genetically from cells of a host.

The term "autologous," as used herein, refers to cells derived from the same subject. The term "engraft" as used herein refers to the process of stem cell incorporation into a tissue of interest in vivo through contact with existing cells of the tissue.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, preferably within 5-fold, and more preferably within 2-fold, of a value. Unless otherwise stated, the term 'about' means within an acceptable error range for the particular value.

As used herein, the term "activated mesesnchymal stem cell" refers to mesenchymal stem cells treated with one or more agents and/or stimuli capable of inducing one or more alterations in the cell: metabolic, immunological, growth factor-secreting, surface marker expression, and/or production of microvesicles. Examples of agents include epidermal growth factor (EGF; (Peprotech), Transforming Growth Factor-alpha (TGF-alpha; Peprotech), basic Fibroblast Growth Factor (bFGF; Peprotech), brain-derived neurotrophic factor (BDNF; R&D Systems), and Keratinocyte Growth Factor (KGF; Peprotech). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. A preferred mitogenic growth factor is EGF. EGF is preferably added to the basal culture medium at a concentration of between 5 and 500 ng/ml or of at least 5 and not higher than 500 ng/ml. A preferred concentration is at least 10, 20, 25, 30, 40, 45, or 50 ng/ml and not higher than 500, 450, 400, 350, 300, 250, 200, 150, or 100 ng/ml. A more preferred concentration is at least 50 and not higher than 100 ng/ml. An even more preferred concentration is about 50 ng/ml or 50 ng/ml. The same concentrations could be used for a FGF, preferably for FGF10 or FGF7. If more than one FGF is used, for example, FGF7 and FGF10, the concentration of a FGF is as defined above and refers to the total concentration of FGF used. During culturing of stem cells, the mitogenic growth factor is preferably added to the culture medium every second day, while the culture medium is refreshed preferably every fourth day. Any member of the bFGF family may be used. In some cases, FGF7 and/or FGF10 is used. FGF7 is also known as KGF (Keratinocyte Growth Factor).

"Cell culture" is an artificial in vitro system containing viable cells, whether quiescent, senescent or (actively) dividing. In a cell culture, cells are grown and maintained at an appropriate temperature, typically a temperature of 37. degree. C. and under an atmosphere typically containing oxygen and CO.sub.2. Culture conditions may vary widely for each cell type though, and variation of conditions for a particular cell type can result in different phenotypes being expressed. The most commonly varied factor in culture systems is the growth medium. Growth media can vary in concentration of one or more of nutrients, growth factors, and the presence of other components. The growth factors used to supplement media are often derived from animal blood, such as calf serum.

As used herein, the term "conditioned medium of fibroblast regenerative cells" refers to a liquid media that has been in contact with cells, wherein the cells produce one or more factors that enter the media, thus bestowing upon the media at least one therapeutic activity.

The term "individual", as used herein, refers to a human or animal that may or may not be housed in a medical facility and may be treated as an outpatient of a medical facility. The individual may or may not be receiving one or more medical compositions from a medical practitioner and/or via the Internet. An individual may comprise any age of a human or non-human animal and therefore includes both adult and juveniles (i.e., children) and infants. It is not intended that the term "individual" connote a need for medical treatment, therefore, an individual may voluntarily or involuntarily be part of experimentation whether clinical or in support of basic science studies. The term "subject" or "individual" refers to any organism or animal subject that is an object of a method and/or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

As used herein, "immune system disease" means any disease mediated by T-cell interactions with B7-positive cells including, but not limited to, autoimmune diseases, graft related disorders and immunoproliferative diseases. Examples of immune system diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis, T-cell lymphoma, T-cell acute lymphoblastic leukemia, testicular angiocentric T-cell lymphoma, benign lymphocytic angiitis, lupus (e.g. lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitis, type I diabetes mellitis, type II diabetes mellitis), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g. rheumatoid arthritis), polymyositis, scleroderma, and mixed connective tissue disease.

As used herein, "subject" includes but is not limited to human, non-human primates (e.g., monkey, ape), sheep, rabbit, pig, dog, cat, mouse, or rat.

As used herein, "tissue transplant" is defined as a tissue of all, or part of, an organ that is transplanted to a recipient subject. In certain embodiments, the tissue is from one or more solid organs. Examples of tissues or organs include, but are not limited to, skin, heart, lung, pancreas, kidney, liver, bone marrow, pancreatic islet cells, pluripotent stem cells, cell suspensions, and genetically modified cells. The tissue can be removed from a donor subject, or can be grown in vitro. The transplant can be an autograft, isograft, allograft, or xenograft, or a combination thereof.

As used herein, "transplant rejection" is defined as the nearly complete, or complete, loss of viable graft tissue from the recipient subject.

As used herein, "encapsulation" is defined as a process that immunoisolates cells and/or cell clusters, which produce and secrete therapeutic substances, e.g. insulin, and to the medical use of these formulations. The encapsulation process involves the placement of the cells and/or cell clusters within a semipermeable membrane barrier prior to transplantation in order to avoid rejection by the immune system. The molecular weight cut-off of the encapsulating membrane can be controlled by the encapsulation procedure so as to exclude inward diffusion of immunoglobulin and lytic factors of the complement system, but allow the passage of smaller molecules such as glucose and insulin. Encapsulation permits the islet cells to respond physiologically to changes in blood glucose but prevents contact with components of the immune system. Methods of encapsulation of pancreatic islet cells are described in U.S. Pat. No. 6,080,412.

As used herein, "ligand" refers to a molecule that specifically recognizes and binds another molecule, for example, a ligand for CTLA4 is a CD80 and/or CD86 molecule.

As used herein, "a soluble ligand which recognizes and binds CD80 and/or CD86 antigen" includes ligands such as CTLA4Ig, CD28Ig or other soluble forms of CTLA4 and CD28; recombinant CTLA4 and CD28; mutant CTLA4 molecules such as L104EA29YIg; and any antibody molecule, fragment thereof or recombinant binding protein that recognizes and binds a CD80 and/or CD86 antigen. These agents are also considered "immunosuppressive agents".

As used herein, "costimulatory pathway" is defined as a biochemical pathway resulting from interaction of costimulatory signals on T cells and antigen presenting cells (APCs). Costimulatory signals help determine the magnitude of an immunological response to an antigen. One costimulatory signal is provided by the interaction with T cell receptors CD28 and CTLA4 with CD80 and/or CD86 molecules on APCs.

As used herein, "CD80 and/or CD86" includes B7-1 (also called CD80). B7-2 (also called CD86), B7-3 (also called CD74), and the B7 family, e.g., a combination of B7-1, B7-2, and/or B7-3.

As used herein, "costimulatory blockade" is defined as a protocol of administering to a subject, one or more agents that interfere or block a costimulatory pathway, as described above. Examples of agents that interfere with the costimulatory blockade include, but are not limited to, soluble CTLA4, mutant CTLA4, soluble CD28, anti-B7 monoclonal antibodies (mAbs), soluble CD40, and anti-gp39 mAbs. In one embodiment, L104EA29YIg is a preferred agent that interferes with the costimulatory blockade.

As used herein, "T cell depleted bone marrow" is defined as bone marrow removed from bone that has been exposed to an anti-T cell protocol. An anti-T cell protocol is defined as a procedure for removing T cells from bone marrow. Methods of selectively removing T cells are well known in the art. An example of an anti-T cell protocol is exposing bone marrow to T cell specific antibodies, such as anti-CD3, anti-CD4, anti-CD5, anti-CD8, and anti-CD90 monoclonal antibodies, wherein the antibodies are cytotoxic to the T cells. Alternatively, the antibodies can be coupled to magnetic particles to permit removal of T cells from bone marrow using magnetic fields. Another example of an anti-T cell protocol is exposing bone marrow T cells to anti-lymphocyte serum or anti-thymocyte globulin.

As used herein, "tolerizing dose of T cell depleted bone marrow" is defined as an initial dose of T cell depleted bone marrow that is administered to a subject for the purpose of inactivating potential donor reactive T cells.

As used herein, "engrafting dose of T cell depleted bone marrow" is defined as a subsequent dose of T cell depleted bone marrow that is administered to a subject for the purpose of establishing mixed hematopoietic chimerism. The engrafting dose of T cell depleted bone marrow will accordingly be administered after the tolerizing dose of T cell depleted bone marrow.

As used herein, "mixed hematopoietic chimerism" is defined as the presence of donor and recipient blood progenitor and mature cells (e.g., blood deriving cells) in the absence (or undetectable presence) of an immune response.

As used herein, "administer" or "administering" to a subject includes but not limited to intravenous (i.v.) administration, intraperitoneal (i.p.) administration, intramuscular (i.m.) administration, subcutaneous administration, oral administration, administration by injection, as a suppository, or the implantation of a slow-release device such as a miniosmotic pump, to the subject.

As used herein, the term "exendin" includes naturally occurring (or synthetic versions of naturally occurring) exendin peptides that are found in the salivary secretions of the Gila monster. Exendins of particular interest include exendin-3 and exendin-4. The exendins, exendin analogs, and exendin agonists for use in the methods described herein may optionally be amidated, and may also be in an acid form, pharmaceutically acceptable salt form, or any other physiologically active form of the molecule. Exendin-4 (HGEGTFTSDLSKQMEEEAVRLFIEW-LKNGGPSSGAPPPS-NH.sub.2 (SEQ ID NO:1)) is a peptide found in the saliva of the Gila monster, Heloderma suspectum; and exendin-3 (HSDGTFTSDLSKQMEEE-AVRLFIEWLKNGGPSSGAPPPS-NH.sub.2 (SEQ ID NO:2)) is a peptide found in the saliva of the beaded lizard, Heloderma horridum. Exendins have some amino acid sequence similarity to some members of the glucagon-like peptide (GLP) family. For example, exendin-4 has about 53% sequence identity with glucagon-like peptide-1(GLP-1)(7-37) (HAEGTFTSDVSSYLEGQAAKEFI-AWLVKGRG (SEQ ID NO:22). However, exendin-4 is transcribed from a distinct gene, not the Gila monster homolog of the mammalian proglucagon gene from which GLP-1 is expressed. Additionally, exendin-4 is not an analog of GLP-1(7-37) because the structure of synthetic exendin-4 peptide was not created by sequential modification of the structure of GLP-1. Nielsen et al, Current Opinion in Investigational Drugs, 4(4):401-405 (2003). Synthetic exendin-4, also known as exenatide, is commercially available as BYETTA® (Amylin Pharmaceuticals, Inc. and Eli Lilly and Company). BYETTA® contains exenatide, a preservative (e.g., metacresol), a tonicity-adjusting agent (e.g., mannitol), and a buffer (e.g., an acetate buffer). A once weekly formulation of exenatide is currently awaiting FDA approval and is described in WO 2005/102293, the disclosure of which is incorporated by reference herein. This once weekly formulation comprises exenatide and biodegradable polymeric (e.g., poly(lactide-co-glycolide)) microspheres, and is referred to herein as EQW (BYDUREON™ by Amylin Pharmaceuticals, Inc., Eli Lilly and Company, Alkermes, Inc.).

As used herein, "Exendin analog" refers to peptides or other compounds which elicit a biological activity of an exendin reference peptide, preferably having a potency equal to or better than the exendin reference peptide (e.g., exendin-4), or within five orders of magnitude (plus or minus) of potency compared to the exendin reference peptide, when evaluated by art-known measures such as receptor binding and/or competition studies as described, e.g., by Hargrove et al, Regulatory Peptides, 141:113-119 (2007), the disclosure of which is incorporated by reference herein. Preferably, the exendin analogs will bind in such assays with an affinity of less than 1. mu.M, and more preferably with an affinity of less than 3 nM, or less than 1 nM. The term "exendin analog" may also be referred to as "exendin agonist". Exendin analogs also include the peptides described herein which have been chemically derivatized or altered, for example, peptides with non-natural amino acid residues (e.g., taurine, .beta.-amino acid residues, .gamma.-amino acid residues, and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid. Exendin analogs may also contain other chemical moieties, such as peptide mimetics. Exemplary exendins and exendin analogs include exendin-4 (SEQ ID NO:1); exendin-3 (SEQ ID NO:2); Leu.sup.14-exendin-4 (SEQ ID NO:3); Leu.sup.14, Phe.sup.25-exendin-4 (SEQ ID NO:4); Leu.sup.14, A1a.sup.19, Phe.sup.25-exendin-4 (SEQ ID NO:5); exendin-4(1-30) (SEQ ID NO:6); Leu-.sup.14-exendin-4(1-30) (SEQ ID NO:7); Leu.sup.14, Phe-.sup.25-exendin-4(1-30) (SEQ ID NO:8); Leu.sup.14, A1a.sup.19, Phe.sup.25-exendin-4(1-30) (SEQ ID NO:9); exendin-4(1-28) (SEQ ID NO:10); Leu.sup.14-exendin-4(1-28) (SEQ ID NO:11); Leu.sup.14, Phe.sup.25-exendin-4(1-28) (SEQ ID NO:12); Leu.sup.14, A1a.sup.19, Phe.sup.25-exendin-4 (1-28) (SEQ ID NO:13); Leu.sup.14, Lys.sup.17, 20, A1a.sup.19, G1u.sup.21, Phe.sup.25, Gln.sup.28-exendin-4 (SEQ ID NO:14); Leu.sup.14, Lys.sup.17,20, A1a.sup.19, Glu.sup.21, Gln.sup.28-exendin-4 (SEQ ID NO:15); octylGlyl.sup.4, Gln.sup.28-exendin-4 (SEQ ID NO:16); Leu.sup.14, Gln.sup.28, octylGly.sup.34-exendin-4 (SEQ ID NO:17); Phe.sup.4, Leu.sup.14, Gln.sup.28, Lys-.sup.33, Glu.sup.34, Ile.sup.35,36, Ser.sup.37-exendin-4(1-37) (SEQ ID NO:18); Phe.sup.4, Leu.sup.14, Lys.sup.17,20, Ala.sup.19, Glu.sup.21, Gln.sup.28-exend-in-4 (SEQ ID NO:19); Val.sup.11, Ile.sup.13, Leu.sup.14, Ala.sup.16, Lys-.sup.21, Phe.sup.25-exendin- -4 (SEQ ID NO:20); exendin-4-Lys.sup.40 (SEQ ID NO:21); lixisenatide (Sanofi-Aventis/Zealand Pharma); CJC-1134 (ConjuChem, Inc.); [N.sup.epsilon.-(17-carboxyheptadecanoic acid)Lys.sup.20] exendin-4-NH.sub.2; [N.sup.epsilon.-(17-carboxyhepta-decanoyl)Lys.sup.32]exendin-4-NH.sub.2; [desamino-His.sup.1, N.sup.epsilon.-(17-carboxyheptadecanoyl) Lys.sup.20]e-xendin-4-NH.sub.2; [Arg.sup.12,27, NLe.sup.14, N.sup.E-(17-carboxy-heptadecanoyl)Lys-.sup.32]ex-endin-4-NH.sub.2; [N.sup.epsilon.-(19-carboxy-nonadecanoylamino)Lys.sup.20]-exendin-4-NH.s-ub.2; [N-(15-carboxypentadecanoylamino)Lys.sup.20]-exendin-4-NH.sub.2; [N.sup.E-(13-carboxytridecanoylamino) Lys.sup.20]exendin-4-NH.sub .2; [N.sup.epsilon.-(11-carboxy-undecanoyl-amino)Lys.sup.20]exendin-4-NH.sub-.2; exendin-4-Lys.sup.40(8-MPA)-NH.sub.2; exendin-4-Lys.sup.40(.epsilon.-AEEA-AEEA-MPA)-NH.sub.2; exendin-4-Lys.sup.40(8-AEEA-MPA)-NH.sub.2; exendin-4-Lys.sup.40(.epsilon.-MPA)-albumin; exendin-4-Lys-.sup.40(8-AEEA-AEEA-MPA)-albumin; exendin-4-Lys-.sup.40(.epsilon.-AEEA-MPA)-albumin; and the like. AEEA refers to [2-(2-amino)ethoxy)]ethoxy acetic acid. EDA refers to ethylenediamine. MPA refers to maleimidopropionic acid. The exendins and exendin analogs may optionally be amidated. Other exendins and exendin analogs useful in the methods described herein include those described in WO 98/05351; WO 99/07404; WO 99/25727; WO 99/25728; WO 99/40788; WO 00/41546; WO 00/41548; WO 00/73331; WO 01/51078; WO 03/099314; U.S. Pat. Nos. 6,956,026; 6,506,724; 6,703,359; 6,858,576; 6,872,700; 6,902,744; 7,157,555; 7,223,725; 7,220,721; U.S. Publication No. 2003/0036504; and U.S. Publication No. 2006/0094652, the disclosures of which are incorporated by reference herein in their entirety.

As used herein, "pharmaceutically acceptable carrier" includes any material which, when combined with the reactive agent, retains the reactive agent's biological activity, e.g., binding specificity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets, including coated tablets and capsules. Typically, such carriers contain excipients, such as starch, milk, sugar, certain types of clay, gelatin, stearic acid or salts, thereof, magnesium or calcium stearate, talc, vegetable fats or oils, gums, glycols, or other known excipients. Such carriers may also include flavor and color additives or other ingredients.

Compositions comprising such carriers are formulated by well-known conventional methods.

As used herein, “immunosuppressive agents” are defined as a composition having one or more types of molecules that prevent the occurrence of an immune response, or weaken a subject’s immune system. Preferably, the agents reduce or prevent T cell proliferation. Some agents may inhibit T cell proliferation by inhibiting interaction of T cells with other antigen presenting cells (APCs). One example of APCs is B cells. Examples of agents that interfere with T cell interactions with APCs, and thereby inhibit T cell proliferation, include, but are not limited to, ligands for CD80 and/or CD86 antigens, ligands for CTLA4 antigen, and ligands for CD28 antigen. Examples of ligands for CD80 and/or CD86 antigens include, but are not limited to, soluble CTLA4, soluble CTLA4 mutant, soluble CD28, or monoclonal antibodies that recognize and bind CD80 and/or CD86 antigens, or fragments thereof. One preferred agent is L104EA29YIg. Ligands for CTLA4 or CD28 antigens include monoclonal antibodies that recognize and bind CTLA4 and/or CD28, or fragments thereof. Other ligands for CTLA4 or CD28 include soluble CD80 and/or CD86 molecules, such as CD80 and/or CD86Ig. Persons skilled in the art will readily understand that other agents or ligands can be used to inhibit the interaction of CD28 with CD80 and/or CD86.

Immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In some embodiments of the invention, therapeutic microvesicles are administered together with a “tolerogenic adjuvant”. In one embodiment tolerogenic adjuvants is low dose interleukin-2. term “low-dose IL-2” refers to the dosage range wherein immune suppressive T cells are preferentially enhanced relative to Tcons. In one embodiment, low-dose IL-2 refers to IL-2 doses that are less than or equal to 50% of the “high-dose IL-2” doses (e.g., 18 million IU per m.sup.2 per day to 20 million IU per m.sup.2 per day, or more) used for anti-cancer immunotherapy. The upper limit of “low-dose IL-2” can further be limited by treatement adverse events, such as fever, chills, asthenia, and fatigue. IL-2 is generally dosed according to an amount measured in international units (IU) administered in comparison to body surface area (BSA) per given time unit. BSA can be calculated by direct measurement or by any number of well-known methods (e.g., the Dubois & Dubois formula), such as those described in the Examples. Generally, IL-2 is administered according in terms of IU per m.sup.2 of BSA per day. Exemplary low-dose IL-2 doses according to the methods of the present invention include, in terms of 10.sup.6 IU/m.sup.2/day, any one of 0.3, 0.4, 0.5, 0.6, 0.7, 0.8, 0.9, 1.0, 1.1, 1.2, 1.3, 1.4, 1.5, 1.6, 1.7, 1.8, 1.9, 2,0, 2.1, 2.2, 2.3, 2.4, 2.5, 2.6, 2.7, 2.8, 2.9, and 3.0.times.10.sup.6 IU/m.sup.2/day, including any values in between and/or ranges in between. For example, an induction regimen dose can range between 0.3.times.10.sup.6 IU/m.sup.2/day and 3.0.times.10.sup.6 IU/m.sup.2/day with any value or range in between.

The term “continuous administration” refers to administration of IL-2 at regular intervals without any intermittent breaks in between. Thus, no interruptions in IL-2 occur. For example, the induction dose can be administered every day (e.g., once or more per day) during at least 1-14 consecutive days or any range in between (e.g., at least 4-7 consecutive days). As described herein, longer acting IL-2 agents and/or IL-2 agents administered by routes other than subcutaneous administration are contemplated. Intermittent intravenous administration of IL-2 described in the art results in short IL-2 half lives incompatible with increasing plasma IL-2 levels and increasing the immune suppressive T cells:Tcons ratio according to the present invention. However, once-daily subcutaneous IL-2 dosing, continuous IV infusion, long-acting subcutaneous IL-2 formulations, and the like are contemplated for achieving a persistent steady state IL-2 level.

As described above, IL-2 can be administered in a pharmaceutically acceptable formulation and by any suitable administration route, such as by subcutaneous, intravenous, intraperitoneal, oral, nasal, transdermal, or intramuscular administration. In one embodiment, the present invention provides pharmaceutically acceptable compositions which compose IL-2 at a therapeutically-effective amount, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

In some embodiments of the invention, said tolerogenic adjuvants are agents that increase T regulatory cell activity and/or number. In one embodiment said tolerogenic adjuvant is rapamycin. In another embodiment, said tolerogenic adjuvant is anti-CD3 antibodies.

For the practice of the invention, it is important to utilize the proper type of anti-CD3 antibody. The natural role of CD3 is to transduce signals in T cells from the T cell receptor into the nucleus of the T cells, usually to activity T cells. In some situations, antibodies to CD3 cause activation of T cells, not suppression. For example, Hirsch et al. investigated the ability of low dose anti-CD3 to enhance an anti-tumor response directed against the malignant murine UV-induced skin tumor. Low dose anti-CD3 administration resulted in enhanced in vitro anti-tumor activity and prevented tumor outgrowth in approximately two-thirds of animals treated at the time of tumor inoculation. Furthermore, these animals displayed lasting tumor-specific immunity. Augmentation of various parameters of immunity was noted. These results suggested that anti-CD3 mAb can be utilized for the enhancement of anti-tumor responses in vivo and may have general application in the treatment of immunodeficiency. They also point to the care that needs to be exercised when manipulating the CD3 pathway, given that the pathway can be both activatory or inhibitory [91].

Activatory signals by crosslinking CD3 are also seen in the tumor infiltrating lymphocyte (TIL) culture systems. It is known that early in the life of the TIL bulk culture, cytotoxicity is non-major histocompatibility complex restricted. Under these culture conditions antitumor cytotoxicity was observed to decline with increasing age of the bulk culture. In addition, TIL became refractory to IL-2-induced expansion. In one study, scientists have used solid-phase anti-CD3 antibodies for TIL activation followed by culture in reduced concentrations of IL-2 to reactivate TIL previously grown in high concentrations of rIL-2. TIL refractory to IL-2 in terms of growth and antitumor cytotoxicity proved sensitive to anti-CD3 activation. The use of solid-phase anti-CD3 was also more effective than high concentrations of IL-2 in the expansion of TIL when used at the start of culture. Finally, TIL could be induced to secrete IL-2 following solid-phase activation with anti-CD3. These data suggest that human TIL are susceptible to activation by signals directed at the CD3 complex of the TIL cell surface [92].

An example of how different CD3 targeting antibodies can elicit different effects is seen in another study, which Davis et al. examined the IgM monoclonal antibody called 38.1, which was distinct from other anti-CD3 mAb, in that it was rapidly modulated from the cell surface in the absence of a secondary antibody. Although 38.1 induced an immediate increase in intracellular free calcium [Ca2+]i by highly purified T cells, it did not induce entry of the cells into the cell cycle in the absence of accessory cells (AC) or a protein kinase C-activating phorbol ester. Treated T cells were markedly inhibited in their capacity to respond to the T cell stimulating mitogen phytohemagluttanin. Inhibition of responsiveness could be overcome by culturing the cells with supplemental antigen presenting cells or the cytokine IL-2. These studies demonstrate that a state of T cell nonresponsiveness can be induced by modulating CD3 with an anti-CD3 mAb in the absence of co-stimulatory signals. A brief increase in [Ca2+]i resulting from mobilization of internal calcium stores appears to be sufficient to induce this state of T cell nonresponsiveness [93].

In some situations, anti-CD3 antibodies have been shown to program T cells towards antigen-specific tolerance. This is illustrated in one example in the work of Anasetti et al. who exposed PBMC to alloantigen for 3-8 d in the presence of anti-CD3 antibodies. They showed no response after restimulation with cells from the original donor but the PBMC remained capable of responding to third-party donors. Antigen-specific nonresponsiveness was induced by both nonmitogenic and mitogenic anti-CD3 antibodies but not by antibodies against CD2, CD4, CD5, CD8, CD18, or CD28. This suggested the unique ability of this protein to modulate programs in the T cells that are antigen specific. Nonresponsiveness induced by anti-CD3 antibody in mixed leukocyte culture was sustained for at least 34 d from initiation of the culture and 26 d after removal of the antibody. Anti-CD3 antibody also induced antigen-specific nonresponsiveness in cytotoxic T cell generation assays. Anti-CD3 antibody did not induce nonresponsiveness in previously primed cells [94].

The use of anti-CD3 antibodies for the practice of the invention requires that the antibodies not only do not result in activation of T cell proliferation and inflammatory cytokine secretion, but also that the T cells actually inhibit inflammation and promote regeneration.

In one embodiment of the invention, anti-CD3 antibody is given 14 days before administration of mesenchymal stem cells In one specific embodiment, said 14-day course of the anti-CD3 monoclonal antibody utilizes the antibody hOKT3γ1(Ala-Ala) administered intravenously (1.42 μg per kilogram of body weight on day 1; 5.67 μg per kilogram on day 2; 11.3 μg per kilogram on day 3; 22.6 μg per kilogram on day 4; and 45.4 μg per kilogram on days 5 through 14); these doses were based on those previously used for treatment of transplant rejection [95] which is incorporated by reference. Other types of anti-CD3 molecules and dosing regimens may be used in the context of ARDS therapeutics, said doses may be chosen from examples of utility of anti-CD3 from the literature, as described in the following papers and incorporated by reference: prevention of kidney [96-104], liver [105-107], pancreas [108-110], lung [111], and heart [112-116] transplant rejection; prevention of graft versus host disease [117], multiple sclerosis [118], type 1 diabetes [119], The use of monoclonal antibodies for the practice of the invention must be tempered by the caution that in some cases cytokine storm may be initiated by antibody administration [120, 121]. In some cases this is concentration dependent [122]. Treatment for this can be accomplished by steroid administration or anti-IL6 antibody [123-127].

In some embodiments of the invention administration of PGE1 and/or various natural anti-inflammatory compounds are provided to decrease TNF-alpha production as a result of anti-CD3 administration, such as described in this paper and incorporated by reference [128]. In further embodiments of the invention, administration of anti-CD3 may be performed together with endothelial protectants and/or anti-coagulants in order to reduce clotting associated with CD3 modulating agents [129]. In some embodiments anti-CD3 antibodies may be used in combination with tolerogenic cytokines such as interleukin-10 in order to enhance number of angiogenesis supporting T cells. The safety of anti-CD3 and IL-10 administration has previously been demonstrated in a clinical trial [130].

In the current invention decreased TNF-alpha activity is correlated with enhancement of pulmonary regenerative activity. Furthermore, other inhibitors of TNF-alpha may be administered [131, 132].

In some embodiments of the invention, enhancement of pulmonary regenerative activity is provided by administration of oral modulators of CD3. Oral administration of OKT3 has been previously performed in a clinical trial and results are incorporated by reference [133, 134].

In one embodiment, MSC exosomes, or particles may be produced by culturing mesenchymal stem cells in a medium to condition it. The mesenchymal stem cells may comprise human umbilical tissue derived cells which possess markers selected from a group comprising of CD90, CD73 and CD105. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or b-mercaptoethanol, or any combination thereof. The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrame. The conditioned medium may be concentrated about 50 times or more. The conditioned medium may be subject to liquid chromatography such as HPLC. The conditioned medium may be separated by size exclusion. Any size exclusion matrix such as Sepharose may be used. As an example, a TSK Guard column SWXL, 6.times.40 mm or a TSK gel G4000 SWXL, 7.8.times.300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The r.sub.h of particles in this peak is about 45-55 nm. Such fractions comprise mesenchymal stem cell particles such as exosomes.

Culture conditioned media may be concentrated by filtering/desalting means known in the art. In one embodiment Amicon filters, or substantially equivalent means, with specific molecular weight cut-offs are utilized, said cut-offs may select for molecular weights higher than 1 kDa to 50 kDa.

The cell culture supernatant may alternatively be concentrated using means known in the art such as solid phase extraction using C18 cartridges (Mini-Spe-ed C18-14%, S.P.E. Limited, Concord ON). Said cartridges are prepared by washing with methanol followed by deionized-distilled water. Up to 100 ml of stem cell or progenitor cell supernatant may be passed through each of these specific cartridges before elution, it is understood of one of skill in the art that larger cartridges may be used. After washing the cartridges material adsorbed is eluted with 3 ml methanol, evaporated under a stream of nitrogen, redissolved in a small volume of methanol, and stored at 4. degree. C.

Before testing the eluate for activity in vitro, the methanol is evaporated under nitrogen and replaced by culture medium. Said C18 cartridges are used to adsorb small hydrophobic molecules from the stem or progenitor cell culture supernatant, and allows for the elimination of salts and other polar contaminants. It may, however be desired to use other adsorption means in order to purify certain compounds from said fibroblast cell supernatant. Said fibroblast concentrated supernatant may be assessed directly for biological activities useful for the practice of this invention, or may be further purified. In one embodiment, said supernatant of fibroblast culture is assessed for ability to stimulate proteoglycan synthesis using an in vitro bioassay. Said in vitro bioassay allows for quantification and knowledge of which molecular weight fraction of supernatant possesses biological activity. Bioassays for testing ability to stimulate proteoglycan synthesis are known in the art. Production of various proteoglycans can be assessed by analysis of protein content using techniques including mass spectrometry, column chromatography, immune based assays such as enzyme linked immunosorbent assay (ELISA), immunohistochemistry, and flow cytometry.

Further purification may be performed using, for example, gel filtration using a Bio-Gel P-2 column with a nominal exclusion limit of 1800 Da (Bio-Rad, Richmond Calif.). Said column may be washed and pre-swelled in 20 mM Tris-HCl buffer, pH 7.2 (Sigma) and degassed by gentle swirling under vacuum. Bio-Gel P-2 material be packed into a 1.5.times.54 cm glass column and equilibrated with 3 column volumes of the same buffer. Amniotic fluid stem cell supernatant concentrates extracted by C18 cartridge may be dissolved in 0.5 ml of 20 mM Tris buffer, pH 7.2 and run through the column. Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry. Administration of supernatant active fractions may be performed locally or systemically.

In one embodiment of the invention therapeutic exosomes are administered together with “tolerogenic adjuvants”. Adjuvants of use may include exenatide, alpha-1-trypsin, nicotinamide [135], aminoguanidine [136], or GM-CSF.

In some embodiments the invention teaches the administration of therapeutic microvesicles as a means of inhibiting autoimmune attack against regenerating islets. It is believed that the pancreatic duct epithelium itself serves as a pool for progenitors for both islet and acinar tissues after birth and into adulthood and, thus, that the duct epithelium can be considered ‘facultative stem cells’ [137-163]. Some believe that the pancreatic ductal epithelium is initially populated by bone marrow derived cells [164-167]. Accordingly, regeneration of islets can be stimulated by administration of cells, different growth factors (such as ilotropin [168], growth hormone [169], insulin [170], prolactin [169, 171], exendin-4 [172-174], GLP-1 [175-179], dapagliflozin [180], Betacellulin [181-183], activin A [184], gastrin [185], EGF [186], IGF-1 [187, 188], IDX-1 [189], reg protein [190-192], neurogenin-3 [193-196], Nidogen-1 [197], HNF-6 [198], SEPT7b [162], SOX-9 [199], heparan sulfate [200], estrogen [201], INGAP [202, 203], ghrelin [204], SDF-1 [205], PDX-1 [204, 206], MAFA [204], thyrotrophin releasing hormone [207], ), or compounds (such as Gymnema sylvestre leaf extracts [208], Nigella Sativa extract [209], probucol [210], astralagus polysaccharides [211], M. charantia (bitter gourd) acetone extract [212], ICA512 [213], flavonoid rich fraction (FRF) of Oreocnide integrifolia leaves [214], Agaricus bisporus lectins [215], ginsenoside Rh2 [216], FTY 720 [217], Tephrosia purpurea extract [218].

In some embodiments therapeutic microvesicles such as exosomes are administered in situations of mixed hematopoietic chimerism to increase chimerism. In some embodiments microvesicles a donor derived.

In some embodiments of the invention administration of therapeutic microvesicles is performed together with cellular therapy for diabetes. In one embodiment cellular therapy comprises administration of islet cells. Protocols for islet cell transplantation are known in the literature and incorporated by reference. In other embodiments regenerative cells are administered together with islets or as a monotherapy [219]. For example, in one paper a nonrandomized, open-label, parallel-armed prospective study was described. MSCs were isolated from umbilical cord (UC) of healthy donors. Fifty-three participants including 33 adult-onset (≥18 years) and 20 juvenile-onset T1D were enrolled. Twenty-seven subjects (MSC-treated group) received an initial systemic infusion of allogeneic UC-MSCs, followed by a repeat course at 3 months, whereas the control group (n=26) only received standard care based on intensive insulin therapy. Data at 1-year follow-up was reported in this study. The primary endpoint was clinical remission defined as a 10% increase from baseline in the level of fasting and/or postprandial C-peptide. The secondary endpoints included side effects, serum levels of HbA1c, changes in fasting and postprandial C-peptide, and daily insulin doses. After 1-year follow-up, 40.7% subjects in MSC-treated group achieved the primary endpoint, significantly higher than that in the control arm. Three subjects in MSC-treated group, in contrast to none in control group, achieved insulin independence and maintained insulin free for 3 to 12 months. Among the adult-onset T1D, the percent change of postprandial C-peptide was significantly increased in MSC-treated group than in the control group. However, changes in fasting or postprandial C-peptide were not significantly different between groups among the juvenile-onset T1D. Multivariable logistic regression assay indicated that lower fasting C-peptide and higher dose of UC-MSC correlated with achievement of clinical remission after transplantation. No severe side effects were observed. It was concluded that one repeated intravenous dose of allogeneic UC-MSCs is safe in people with recent-onset T1D and may result in better islet β cell preservation during the first year after diagnosis compared to standard treatment alone [220].

The invention includes pharmaceutical compositions for use in the treatment of type 1 diabetes and other autoimmune diseases comprising pharmaceutically effective amounts of immune modulatory microvesicles. In some embodiments said microvesicles are administered together with soluble CTLA4 mutant molecules. In certain embodiments, the immune system diseases are mediated by CD28- and/or CTLA4-positive cell interactions with CD80 and/or CD86 positive cells. The soluble CTLA4 molecules are preferably soluble CTLA4 molecules with wildtype sequence and/or soluble CTLA4 molecules having one or more mutations in the extracellular domain of CTLA4. The pharmaceutical composition can include soluble CTLA4 or CTLA4 mutant protein molecules and/or nucleic acid molecules, and/or vectors encoding the molecules. In a preferred embodiment, the soluble CTLA4 mutant molecule has the amino acid sequence of the extracellular domain of CTLA4 as shown in either FIG. 3 (L104EA29Y). Even more preferably, the soluble CTLA4 mutant molecule is L104EA29YIg as disclosed herein shown in FIG. 3. The compositions may additionally include other therapeutic agents, including, but not limited to, immunosuppressive agents, NSAIDs, corticosteroids, glucococoticoids, drugs, toxins, enzymes, antibodies, or conjugates. An embodiment of the pharmaceutical composition comprises an effective amount of a therapeutic microvesicles alone or in combination with an effective amount of at least one other therapeutic agent, including an immunosuppressive agent, or NSAID. Effective amounts of the therapeutic microvesicle in the pharmaceutical composition can range about 0.1 pg to 100 mg/kg weight of the subject. In another embodiment, the effective amount can be an amount about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, or about 95 to 100 mg/kg weight of a subject. In an embodiment, the effective amount is 2 mg/kg weight of a subject. In another embodiment, the effective amount is 10 mg/kg weight of a subject. In an embodiment, the effective amount of a soluble CTLA4 molecule is 2 mg/kg weight of a subject. In an embodiment, the effective amount of a soluble CTLA4 molecule is 10 mg/kg weight of a subject. The amount of an immunosuppressive agent administered to a subject varies depending on several factors including the efficacy of the drug on a specific subject and the toxicity (i.e. the tolerability) of a drug to a specific subject. Methotrexate is commonly administered in an amount about 0.1 to 40 mg per week with a common dosage ranging about 5 to 30 mg per week. Methotrexate may be administered to a subject in various increments: about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, an effective amount of an immunosuppressive agent, including methotrexate, is an amount about 10 to 30 mg/week. Effective amounts of methotrexate range about 0.1 to 40 mg/week. In one embodiment, the effective amount is ranges about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, methotrexate is administered in an amount ranging about 10 to 30 mg/week. Cyclophosphamide, an alkylating agent, may be administered in dosages ranging about 1 to 10 mg/kg body weight per day. Cyclosporine (e.g. NEORAL.sup.R) also known as Cyclosporin A, is commonly administered in dosages ranging from about 1 to 10 mg/kg body weight per day. Dosages ranging about 2.5 to 4 mg per body weight per day are commonly used. Chloroquine or hydroxychloroquine (e.g. PLAQUENIL.sup.R), is commonly administered in dosages ranging about 100 to 1000 mg daily. Preferred dosages range about 200-600 mg administered daily. Sulfasalazine (e.g., AZULFIDINE EN-tabs.sup.R) is commonly administered in amounts ranging about 50 to 5000 mg per day, with a common dosage of about 2000 to 3000 mg per day for adults. Dosages for children are commonly about 5 to 100 mg/kg of body weight, up to 2 grams per day. Gold salts are formulated for two types of administration: injection or oral. Injectable gold salts are commonly prescribed in dosages about 5 to 100 mg doses every two to four weeks. Orally administered gold salts are commonly prescribed in doses ranging about 1 to 10 mg per day. D-penicillamine or penicillamine (CUPRIMINE.sup.R) is commonly administered in dosages about 50 to 2000 mg per day, with preferred dosages about 125 mg per day up to 1500 mg per day. Azathioprine is commonly administered in dosages of about 10 to 250 mg per day. Preferred dosages range about 25 to 200 mg per day. Anakinra (e.g. KINERET-.sup.R) is an interleukin-1 receptor antagonist. A common dosage range for anakinra is about 10 to 250 mg per day, with a recommended dosage of about 100 mg per day. Infliximab (REMICADE.sup.R) is a chimeric monoclonal antibody that binds to tumor necrosis factor alpha (TNF.alpha.). Infliximab is commonly administered in dosages about 1 to 20 mg/kg body weight every four to eight weeks. Dosages of about 3 to 10 mg/kg body weight may be administered every four to eight weeks depending on the subject. Etanercept (e.g. ENBREL.sup.R) is a dimeric fusion protein that binds the tumor necrosis factor (TNF) and blocks its interactions with TNF receptors. Commonly administered dosages of etanercept are about 10 to 100 mg per week for adults with a preferred dosage of about 50 mg per week. Dosages for juvenile subjects range about 0.1 to 50 mg/kg body weight per week with a maximum of about 50 mg per week.

Leflunomide (ARAVA.sup.R) is commonly administered at dosages about 1 and 100 mg per day. A common daily dosage is about 10 to 20 mg per day. The pharmaceutical compositions also preferably include suitable carriers and adjuvants which include any material which when combined with the molecule of the invention (e.g., a soluble CTLA4 mutant molecule, e.g., L104EA29YIg) retains the molecule's activity and is non-reactive with the subject's immune system. Examples of suitable carriers and adjuvants include, but are not limited to, human serum albumin; ion exchangers; alumina; lecithin; buffer substances, such as phosphates; glycine; sorbic acid; potassium sorbate; and salts or electrolytes, such as protamine sulfate. Other examples include any of the standard pharmaceutical carriers such as a phosphate buffered saline solution; water; emulsions, such as oil/water emulsion; and various types of wetting agents. Other carriers may also include sterile solutions; tablets, including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The pharmaceutical compositions of the invention can be administered using conventional modes of administration including, but not limited to, intravenous (i.v.) administration, intraperitoneal (i.p.) administration, intramuscular (i.m.) administration, subcutaneous administration, oral administration, administration as a suppository, or as a topical contact, or the implantation of a slow-release device such as a miniosmotic pump, to the subject.

The pharmaceutical compositions of the invention may be in a variety of dosage forms, which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient.

The invention provides novel compositions of matter for treatment of type 1 diabetes. This includes microvesicles derived from various cell types, methods of manufacture, and therapeutic uses. Provided are means of exosomes derived from myeloid cells reprogrammed by regenerative cells in which said myeloid cells possess regenerative, immune modulatory, anti-inflammatory, and angiogenic/neurogenic activity after culture or exposure to conditioned media from regenerative cells. One type of regenerative cell useful for the current invention is derived from umbilical cord tissue such as Wharton's Jelly. In some embodiments manipulation of stem cell "potency" is disclosed through hypoxic manipulation, growth on non-xenogeneic conditions, as well as addition of epigenetic modulators.

The regenerative cells of the invention may be cultured under hypoxia, in one embodiment, cultured in order to induce and/or augment expression of chemokine receptors. One such receptor is CXCR-4. The population of cells, including population of umbilical cord mesenchymal cells, may be enriched for CXCR-4, such as (or such as about) 50%, 55%, 60%, 65%, 70%, 75%, 80%, 85%, 90%, 95%, 96%, 97%, 98%, 99%, or more of the population expressing CXCR-4, CD31, CD34, or any combination thereof. In addition or alternatively, <1%, <2%, <3%, <4%, <5%, <6%, <7%, <8%, <9%, or <10% of the population of cells may express CD14 and/or CD45. The umbilical cord cells of the invention may further possess markers selected from the group consisting of STRO-1, CD105, CD54, CD56, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1, and a combination thereof. In some embodiments said placental cells of the invention are admixed with endothelial cells. Said endothelial cells may express one or more markers selected from the group consisting of: a) extracellular vimentin; b) CD133; c) c-kit; d) VEGF receptor; e) activated protein C receptor; and f) a combination thereof. In some embodiments, the population of endothelial cells comprises endothelial progenitor cells. Rhe population of cells may be allogeneic, autologous, or xenogenic to an individual, including an individual being administered the population of cells. In some embodiments, the population of cells are matched by mixed lymphocyte reaction matching.

The generation of dendritic cells, which have been conditioned by exposure to culture supernatant of regenerative cells such as mesenchymal stem cells is disclosed in the current invention. In one embodiment the invention teaches that dendritic cells can be utilized after reprogramming but in some situations before reprogramming they may be pulsed with antigens. Dendritic cell technologies are disclosed in the following papers and incorporated by reference. [221-345].

In some embodiments, the population of cells is derived from tissue selected from the group consisting of the placental body, placenta, umbilical cord tissue, peripheral blood, hair follicle, cord blood, Wharton's Jelly, menstrual blood, endometrium, skin, omentum, amniotic fluid, and a combination thereof. In some embodiments, the population of cells, the population of umbilical mesenchymal stem cells, or the population of endothelial cells comprises human umbilical cord derived adherent cells. The human umbilical cord derived adherent cells may express a cytokines selected from the group consisting of) FGF-1; b) FGF-2; c) HGF; d) interleukin-1 receptor antagonist; and e) a combination thereof. In some embodiments, the population of cells, the population of umbilical cord cells express arginase, indoleamine 2,3 deoxygenase, interleukin-10, and/or interleukin 35. In some embodiments, the population of cells, the population of umbilical cord cells, or the population of endothelial cells express hTERT and Oct-4 but does not express a STRO-1 marker.

In some embodiments, the population of cells, the population of umbilical cord cells has an ability to undergo cell division in less than 36 hours in a growth medium. In some embodiments, the population of cells, the population of umbilical cord cells has an ability to proliferate at a rate of 0.9-1.2 doublings per 36 hours in growth media. In some embodiments, the population of cells, the population of umbilical cord cells has an ability to proliferate at a rate of 0.9, 1.0, 1.1, or 1.2 doublings per 36 hours in growth media. The population of cells, population of umbilical cord cells may produce exosomes capable of inducing more than 50% proliferation when the exosomes are cultured with human umbilical cord endothelial cells. The induction of proliferation may occur when the exosomes are cultured with the human umbilical cord endothelial cells at a concentration of 10, 20, 30, 40, 50, 60, 70, 80, 90, 100, 110, 120, 130, 140, 150, 160, 170, 180, 190, 200, or more exosomes per cell.

In some embodiments, a population of cells, including a population of umbilical cells alone, are administered to an individual, including an individual having and acute or chronic pathology, wherein the population of cells may be administered via any suitable route, including as non-limiting examples, intramuscularly and/or intravenously.

In some embodiments, a population of umbilical cord cells is optionally obtained, the population is then optionally contacted via culturing with a population of progenitor for T regulatory cells, wherein the culturing conditions allow for the generation of T regulatory cells, then the generated T regulatory cells are administered to an individual.

In another embodiment of the invention, biologically useful immune cells are generated after culture with regenerative cells, and/or stem cells are disclosed, of the mesenchymal or related lineages, which are therapeutically reprogrammed cells having minimal oxidative damage and telomere lengths that compare favorably with the telomere lengths of undamaged, pre-natal or embryonic stem cells (that is, the therapeutically reprogrammed cells of the present invention possess near prime physiological state genomes). Moreover the therapeutically reprogrammed cells of the present invention are immunologically privileged and therefore suitable for therapeutic applications. Additional methods of the present invention provide for the generation of hybrid stem cells. Furthermore, the present invention includes related methods for maturing stem cells made in accordance with the teachings of the present invention into specific host tissues. For use in the current invention, the practitioner is thought that ontogeny of mammalian development provides a central role for stem cells. Early in embryogenesis, cells from the proximal epiblast destined to become germ cells (primordial germ cells) migrate along the genital ridge. These cells express high levels of alkaline phosphatase as well as expressing the transcription factor Oct4. Upon migration and colonization of the genital ridge, the primordial germ cells undergo differentiation into male or female germ cell precursors (primordial sex cells). For the purpose of this invention disclosure, only male primordial sex cells (PSC) will be discussed, but the qualities and properties of male and female primordial sex cells are equivalent and no limitations are implied. During male primordial sex cell development, the primordial stem cells become closely associated with precursor sertoli cells leading to the beginning of the formation of the seminiferous cords. When the primordial germ cells are enclosed in the seminiferous cords, they differentiate into gonocytes that are mitotically quiescent. These gonocytes divide for a few days followed by arrest at G0/G1 phase of the cell cycle. In mice and rats these gonocytes resume division within a few days after birth to generate spermatogonial stem cells and eventually undergo differentiation and meiosis related to spermatogenesis. It is known that embryonic stem cells are cells derived from the inner cell mass of the pre-implantation blastocyst-stage embryo and have the greatest differentiation potential, being capable of giving rise to cells found in all three germ layers of the embryo proper. From a practical standpoint, embryonic stem cells are an artifact of cell culture since, in their natural epiblast environment, they only exist transiently during embryogenesis. Manipulation of embryonic stem cells in vitro has lead to the generation and differentiation of a wide range of cell types, including cardiomyocytes, hematopoietic cells, endothelial cells, nerves, skeletal muscle, chondrocytes, adipocytes, liver and pancreatic islets. Growing embryonic stem cells in co-culture with mature cells can influence and initiate the differentiation of the embryonic stem cells to a particular lineage. Maturation is a process of coordinated steps either forward or backward in the differentiation pathway and can refer to both differentiation and/or dedifferentiation. In one example of the maturation process, a cell, or group of cells, interacts with its cellular environment during embryogenesis and organogenesis. As maturation progresses, cells begin to form niches and these niches, or microenvironments, house stem cells that direct and regulate organogenesis. At the time of birth, maturation has progressed such that cells and appropriate cellular niches are present for the organism to function and survive post-natally. Developmental processes are highly conserved amongst the different species allowing maturation or differentiation systems from one mammalian species to be extended to other mammalian species in the laboratory. During the lifetime of an organism, the cellular composition of the organs and organs systems are exposed to a wide range of intrinsic and extrinsic factors that induce cellular or genomic damage. Ultraviolet light not only has an effect on normal skin cells but also on the skin stem cell population. Chemotherapeutic drugs used to treat cancer have a devastating effect on hematopoietic stem cells. Reactive oxygen species, which are the byproducts of cellular metabolism, are intrinsic factors that compromises the genomic integrity of the cell. In all organs or organ systems, cells are continuously being replaced from stem cell populations. However, as an organism ages, cellular damage accumulates in these stem cell populations. If the damage is inheritable, such as genomic mutations, then all progeny will be effected and thus compromised. A single stem cell clone can contribute to generations of lineages such as lymphoid and myeloid cells for more than a year and therefore have the potential to spread mutations if the stem cell is damaged. The body responds to a compromised stem cell by inducing apoptosis thereby removing it from the pool and preventing potentially dysfunctional or tumorigenic properties. Apoptosis removes compromised cells from the population, but it also decreases the number of stem cells that are available for the future. Therefore, as an organism ages, the number of stem cells decrease. In addition to the loss of the stem cell pool, there is evidence that aging decreases the efficiency of the homing mechanism of stem cells. Telomeres are the physical ends of chromosomes that contain highly conserved, tandemly repeated DNA sequences. Telomeres are involved in the replication and stability of linear DNA molecules and serve as counting mechanism in cells; with each round of cell division the length of the telomeres shortens and at a pre-determined threshold, a signal is activated to initiate cellular senescence. Stem cells and somatic cells produce telomerase, which inhibits shortening of telomeres, but their telomeres still progressively shorten during aging and cellular stress. In one teaching, or embodiment, of the invention, therapeutically reprogrammed cells, in some embodiments mesenchymal stem cells, are provided. Therapeutic reprogramming refers to a maturation process wherein a stem cell is exposed to stimulatory factors according the teachings of the present invention to yield enhanced therapeutic activity. In some embodiments, enhancement of therapeutic activity may be increase proliferation, in other embodiments, it may be enhanced chemotaxis. Other therapeutic characteristics include ability to under resistance to apoptosis, ability to overcome senescence, ability to differentiate into a variety of different cell types effectively, and ability to secrete therapeutic growth factors which enhance viability/activity, of endogenous stem cells. In order to induce therapeutic reprogramming of cells, in some cases, as disclosed herein, of wharton's jelly originating cells, the invention teaches the utilization of stimulatory factors, including without limitation, chemicals, biochemicals and cellular extracts to change the epigenetic programming of cells. These stimulatory factors induce, among other results, genomic methylation changes in the donor DNA. Embodiments of the present invention include methods for preparing cellular extracts from whole cells, cytoplasts, and karyplasts, although other types of cellular extracts are contemplated as being within the scope of the present invention. In a non-limiting example, the cellular extracts of the present invention are prepared from stem cells, specifically embryonic stem cells. Donor cells are incubated with the chemicals, biochemicals or cellular extracts for defined periods of time, in a non-limiting example for approximately one hour to approximately two hours, and those reprogrammed cells that express embryonic stem cell markers, such as Oct4, after a culture period are then ready for transplantation, cryopreservation or further maturation. In another embodiment of the present invention, hybrid stem cells are provided which can be used for cellular regenerative/reparative therapy. The hybrid stem cells of the present invention are pluripotent and customized for the intended recipient so that they are immunologically compatible with the recipient. Hybrid stem cells are a fusion product between a donor cell, or nucleus thereof, and a host cell. Typically the fusion occurs between a donor nucleus and an enucleated host cell. The donor cell can be any diploid cell, including but not limited to, cells from pre-embryos, embryos, fetuses and post-natal organisms. More specifically, the donor cell can be a primordial sex cell, including but not limited to, oogonium or differentiated or undifferentiated spermatogonium, or an embryonic stem cell. Other non-limiting examples of donor cells are therapeutically reprogrammed cells, embryonic stem cells, fetal stem cells and multipotent adult progenitor cells. Preferably the donor cell has the phenotype of the intended recipient. The host cell can be isolated from tissues including, but not limited to, pre-embryos, embryos, fetuses and post-natal organisms and more specifically can include, but is not limited to, embryonic stem cells, fetal stem cells, multipotent adult progenitor cells and adipose-derived stem cells. In a non-limiting example, cultured cell lines can be used as donor cells. The donor and host cells can be from the same individual or different individuals. In one embodiment of the present invention, lymphocytes are used as donor cells and a two-step method is used to purify the donor cells. After the tissues was disassociated, an adhesion step was performed to remove any possible contaminating adherent cells followed by a density gradient purification step. The majority of lymphocytes are quiescent (in G0 phase) and therefore can have a methylation status than conveys greater plasticity for reprogramming. Multipotent or pluripotent stem cells or cell lines useful as donor cells in embodiments of the present invention are functionally defined as stem cells by their ability to undergo differentiation into a variety of cell types including, but not limited to, adipogenic, neurogenic, osteogenic, chondrogenic and cardiogenic cell.

In some embodiments, host cell enucleation for the generation of hybrid stem cells according to the teachings of the present invention can be conducted using a variety of means. In a non-limiting example, ADSCs were plated onto fibronectin coated tissue culture slides and treated with cells with either cytochalasin D or cytochalasin B. After treatment, the cells can be trypsinized, re-plated and are viable for about 72 hours post enucleation. Host cells and donor nuclei can be fused using one of a number of fusion methods known to those of skill in the art, including but not limited to electrofusion, microinjection, chemical fusion or virus-based fusion, and all methods of cellular fusion are envisioned as being within the scope of the present invention. The hybrid stem cells made according to the teachings of the present invention possess surface antigens and receptors from the enucleated host cell but has a nucleus from a developmentally younger cell. Consequently, the hybrid stem cells of the present invention will be receptive to cytokines, chemokines and other cell signaling agents, yet possess a nucleus free from age-related DNA damage. The therapeutically reprogrammed cells and hybrid stem cells made in accordance with the teachings of the present invention are useful in a wide range of therapeutic applications for cellular regenerative/reparative therapy. For example, and not intended as a limitation, the therapeutically reprogrammed cells and hybrid stem cells of the present invention can be used to replenish stem cells in animals whose natural stem cells have been depleted due to age or ablation therapy such as cancer radiotherapy and chemotherapy. In another non-limiting example, the therapeutically reprogrammed cells and hybrid stem cells of the present invention are useful in organ regeneration and tissue repair. In one embodiment of the present invention, therapeutically reprogrammed cells and hybrid stem cells can be used to reinvigorate damaged muscle tissue including dystrophic muscles and muscles damaged by ischemic events such as myocardial infarcts. In another embodiment of the present invention, the therapeutically reprogrammed cells and hybrid stem cells disclosed herein can be used to ameliorate scarring in animals, including humans, following a traumatic injury or surgery. In this embodiment, the therapeutically reprogrammed cells and hybrid stem cells of the present invention are administered systemically, such as intravenously, and migrate to the site of the freshly traumatized tissue recruited by circulating cytokines secreted by the damaged cells. In another embodiment of the present invention, the therapeutically reprogrammed cells and hybrid stem cells can be administered locally to a treatment site in need or repair or regeneration.

In one embodiment, umbilical cord samples were obtained following the delivery of normal term babies with Institutional Review Board approval. A portion of the umbilical cord was then cut into approximately 3 cm long segments. The segments were then placed immediately into 25 ml of phosphate buffered saline without calcium and magnesium (PBS) and 1.times. antibiotics (100 U/ml penicillin, 100 ug/ml streptomycin, 0.025 ug/ml amphotericin B). The tubes were then brought to the lab for dissection within 6 hours. Each 3 cm umbilical cord segment was dissected longitudinally utilizing aseptic technique. The tissue was carefully undermined and the umbilical vein and both umbilical arteries were removed. The remaining segment was sutured inside out and incubated in 25 ml of PBS, 1.times. antibiotic, and 1 mg/ml of collagenase at room temperature. After 16-18 hours the remaining suture and connective tissue was removed and discarded. The cell suspension was separated equally into two tubes, the cells were washed 3.times. by diluting with PBS to yield a final volume of 50 ml per tube, and then centrifuged. Red blood cells were then lysed using a hypotonic solution. Cells were plated onto 6-well plates at a concentration of 5-20.times.10.sup.6 cells per well. UC-MSC were cultured in low-glucose DMEM (Gibco) with 10% FBS (Hyclone), 2 mM L-Glutamine (Gibco), 100 U/ml penicillin, 100 ug/ml streptomycin, 0.025 ug/ml amphotericin B (Gibco). Cells were washed 48 hours after the initial plating with PBS and given fresh media. Cell culture media were subsequently changed twice a week through half media changes. After 7 days or approximately 70-80% confluence, cells were passed using HyQTase (Hyclone) into a 10 cm plate. Cells were then regularly passed 1:2 every 7 days or upon reaching 80% confluence. Alternatively, 0.25% HQ trypsin/EDTA (Hyclone) was used to passage cells in a similar manner.

In some embodiments of the invention, administration of cells of the invention is performed for suppression of an inflammatory and/or autoimmune disease. In these situations, it may be necessary to utilize an immune suppressive/ or therapeutic adjuvant. Immune suppressants are known in the art and can be selected from a group comprising of: cyclosporine, rapamycin, campath-1H, ATG, Prograf, anti IL-2r, MMF, FTY, LEA, cyclosporin A, diftitox, denileukin, levamisole, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, and trimetrexate), purine analogs (e.g., cladribine, fludarabine, 6-mercaptopurine, thiamiprine, and thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, and tegafur) fluocinolone, triaminolone, anecortave acetate, fluorometholone, medrysone, prednislone, etc. In another embodiment, the use of stem cell conditioned media may be used to potentiate an existing anti-inflammatory agent. Anti-inflammatory agents may comprise one or more agents including NSAIDs, interleukin-1 antagonists, dihydroorotate synthase inhibitors, p38 MAP kinase inhibitors, TNF-α inhibitors, TNF-α sequestration agents, and methotrexate. More specifically, anti-inflammatory agents may comprise one or more of, e.g., anti-TNF-α, lysophylline, alpha 1-antitrypsin (AAT), interleukin-10 (IL-10), pentoxyfilline, COX-2 inhibitors, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (eg., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), epsilon.-acetamidocaproic acid, s-adenosylmethionine, 3-amino-4-hydroxybutyric .acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, candelilla wax, alpha bisabolol, aloe vera, Manjistha, Guggal, kola extract, chamomile, sea whip extract, glycyrrhetic acid, glycyrrhizic acid, oil soluble licorice extract, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid.

References

1. Foulis, A. K., *The pathology of the endocrine pancreas in type 1 (insulin-dependent) diabetes mellitus*. APMIS, 1996. 104(3): p. 161-7.
2. Cudworth, A. G., *Type I diabetes mellitus*. Diabetologia, 1978. 14(5): p. 281-91.
3. Kolb, H., *Benign versus destructive insulitis*. Diabetes Metab Rev, 1997. 13(3): p. 139-46.
4. Coutant, R., et al., *Insulin and the prevention of insulin-dependent diabetes mellitus*. Diabetes Metab, 1997. 23 Suppl 3: p. 25-8.
5. Schranz, D. B. and A. Lernmark, *Immunology in diabetes: an update*. Diabetes Metab Rev, 1998. 14(1): p. 3-29.
6. Rabinovitch, A. and J. S. Skyler, *Prevention of type 1 diabetes*. Med Clin North Am, 1998. 82(4): p. 739-55.
7. Green, E. A. and R. A. Flavell, *Tumor necrosis factor-alpha and the progression of diabetes in non-obese diabetic mice*. Immunol Rev, 1999. 169: p. 11-22.
8. Heinze, E. and A. Thon, *Honeymoon period in insulin-dependent diabetes mellitus*. Pediatrician, 1983. 12(4): p. 208-12.
9. Powers, A. C. and G. S. Eisenbarth, *Autoimmunity to islet cells in diabetes mellitus*. Annu Rev Med, 1985. 36: p. 533-44.
10. Boitard, C., M. Debray-Sachs, and J. F. Bach, *Autoimmune disorders in diabetes*. Adv Nephrol Necker Hosp, 1986. 15: p. 281-305.
11. Nerup, J., et al., *Mechanisms of pancreatic beta-cell destruction in type I diabetes*. Diabetes Care, 1988. 11 Suppl 1: p. 16-23.
12. Dotta, F. and G. S. Eisenbarth, *Type I diabetes mellitus: a predictable autoimmune disease with interindividual variation in the rate of beta cell destruction*. Clin Immunol Immunopathol, 1989. 50(1 Pt 2): p. S85-95.
13. Torn, C., *C-peptide and autoimmune markers in diabetes*. Clin Lab, 2003. 49(1-2): p. 1-10.

14. Vardi, P., et al., *Islet cell autoantibodies: pathobiology and clinical applications*. Diabetes Care, 1987. 10(5): p. 645-56.

15. Rossini, A. A., J. P. Mordes, and D. L. Greiner, *The pathogenesis of autoimmune diabetes mellitus*. Curr Opin Immunol, 1989. 2(4): p. 598-603.

16. Scherbaum, W. A., *Etiology and pathogenesis of type 1 diabetes*. Horm Metab Res Suppl, 1992. 26: p. 111-6.

17. Pankewycz, O. G., J. X. Guan, and J. F. Benedict, *Cytokines as mediators of autoimmune diabetes and diabetic complications*. Endocr Rev, 1995. 16(2): p. 164-76.

18. Winter, W. E., *Type I insulin-dependent diabetes mellitus: a model for autoimmune polygenic disorders*. Adv Dent Res, 1996. 10(1): p. 81-7.

19. Foulis, A. K., C. L. *Oakley lecture* (1987). *The pathogenesis of beta cell destruction in type I (insulin-dependent) diabetes mellitus*. J Pathol, 1987. 152(3): p. 141-8.

20. Falcone, M. and N. Sarvetnick, *The effect of local production of cytokines in the pathogenesis of insulin-dependent diabetes mellitus*. Clin Immunol, 1999. 90(1): p. 2-9.

21. Suri, A. and J. D. Katz, *Dissecting the role of CD4+ T cells in autoimmune diabetes through the use of TCR transgenic mice*. Immunol Rev, 1999. 169: p. 55-65.

22. Masteller, E. L. and J. A. Bluestone, *Immunotherapy of insulin-dependent diabetes mellitus*. Curr Opin Immunol, 2002. 14(5): p. 652-9.

23. Rosmalen, J. G., et al., *Islet abnormalities in the pathogenesis of autoimmune diabetes*. Trends Endocrinol Metab, 2002. 13(5): p. 209-14.

24. Hyoty, H. and K. W. Taylor, *The role of viruses in human diabetes*. Diabetologia, 2002. 45(10): p. 1353-61.

25. Petrovsky, N., D. Silva, and D. A. Schatz, *Prospects for the prevention and reversal of type 1 diabetes mellitus*. Drugs, 2002. 62(18): p. 2617-35.

26. Roep, B. O., *Autoreactive T cells in endocrine/organ-specific autoimmunity: why has progress been so slow?* Springer Semin Immunopathol, 2002. 24(3): p. 261-71.

27. Jun, H. S. and J. W. Yoon, *A new look at viruses in type 1 diabetes*. Diabetes Metab Res Rev, 2003. 19(1): p. 8-31.

28. Gu, D., et al., *The role of infiltrating macrophages in islet destruction and regrowth in a transgenic model*. J Autoimmun, 1995. 8(4): p. 483-92.

29. Boumaza, I., et al., *Autologous bone marrow-derived rat mesenchymal stem cells promote PDX-1 and insulin expression in the islets, alter T cell cytokine pattern and preserve regulatory T cells in the periphery and induce sustained normoglycemia*. J Autoimmun, 2009. 32(1): p. 33-42.

30. Zhao, Y., et al., *Reversal of type 1 diabetes via islet beta cell regeneration following immune modulation by cord blood-derived multipotent stem cells*. BMC Med, 2012. 10: p. 3.

31. Hire, K., et al., *FoxP3+, and not CD25+, T cells increase post-transplant in islet allotransplant recipients following anti-CD25+ rATG immunotherapy*. Cell Immunol, 2012. 274(1-2): p. 83-8.

32. Marek-Trzonkowska, N., et al., *Therapy of type 1 diabetes with CD4(+)CD25(high)CD127-regulatory T cells prolongs survival of pancreatic islets—results of one year follow-up*. Clin Immunol, 2014. 153(1): p. 23-30.

33. Froud, T., et al., *Islet transplantation in type 1 diabetes mellitus using cultured islets and steroid-free immunosuppression: Miami experience*. Am J Transplant, 2005. 5(8): p. 2037-46.

34. Pascher, A. and J. Klupp, *Biologics in the treatment of transplant rejection and ischemia/reperfusion injury: new applications for TNFalpha inhibitors?* BioDrugs, 2005. 19(4): p. 211-31.

35. Li, L., et al., *Autologous hematopoietic stem cell transplantation modulates immunocompetent cells and improves beta-cell function in Chinese patients with new onset of type 1 diabetes*. J Clin Endocrinol Metab, 2012. 97(5): p. 1729-36.

36. Koulmanda, M., et al., *Alpha 1-antitrypsin reduces inflammation and enhances mouse pancreatic islet transplant survival*. Proc Natl Acad Sci USA, 2012. 109(38): p. 15443-8.

37. Zoso, A., et al., *G-CSF and Exenatide Might Be Associated with Increased Long-Term Survival of Allogeneic Pancreatic Islet Grafts*. PLoS One, 2016. 11(6): p. e0157245.

38. Zorina, T. D., et al., *Recovery of the endogenous beta cell function in the NOD model of autoimmune diabetes*. Stem Cells, 2003. 21(4): p. 377-88.

39. Yagi Mendoza, H., et al., *Regeneration of insulin producing islets from dental pulp stem cells using a 3D culture system*. Regen Med, 2018. 13(6): p. 673-687.

40. Harwood, C. H. and C. V. Cook, *Cyclosporine in transplantation*. Heart Lung, 1985. 14(6): p. 529-40.

41. Feutren, G., et al., *Cyclosporin increases the rate and length of remissions in insulin-dependent diabetes of recent onset. Results of a multicentre double-blind trial*. Lancet, 1986. 2(8499): p. 119-24.

42. Dupre, J., C. R. Stiller, and M. Gent, *Immunosuppression and type I diabetes*. Lancet, 1987. 1(8533): p. 634.

43. Colman, P. G. and G. S. Eisenbarth, *Immunotherapy in type I diabetes. Approaches to prevention and treatment*. Postgrad Med, 1987. 81(6): p. 146-55.

44. Boitard, C., et al., *Effect of cyclosporin A treatment on the production of antibody in insulin-dependent (type I) diabetic patients*. J Clin Invest, 1987. 80(6): p. 1607-12.

45. Dupre, J. and C. R. Stiller, *Effects of immunosuppression with cyclosporine on beta cell function and clinical remission in very early overt type I diabetes*. Adv Exp Med Biol, 1988. 246: p. 347-55.

46. Dupre, J., et al., *Effects of immunosuppression with cyclosporine in insulin-dependent diabetes mellitus of recent onset: the Canadian open study at 44 months*. Transplant Proc, 1988. 20(3 Suppl 4): p. 184-92.

47. Debray-Sachs, M., et al., *Inhibition of insulin release in vitro mediated by mononuclear cells from diabetic patients treated with cyclosporin A or placebo*. Diabetes, 1988. 37(7): p. 873-7.

48. *Cyclosporin-induced remission of IDDM after early intervention. Association of 1 yr of cyclosporin treatment with enhanced insulin secretion. The Canadian-European Randomized Control Trial Group*. Diabetes, 1988. 37(11): p. 1574-82.

49. Dupre, J., et al., *Clinical trials of cyclosporin in IDDM*. Diabetes Care, 1988. 11 Suppl 1: p. 37-44.

50. Chatenoud, L., et al., *Effect of cyclosporin on interleukin 2-related T-lymphocyte parameters in IDDM patients*. Diabetes, 1989. 38(2): p. 249-56.

51. Muller, C., et al., *Effects of cyclosporin A upon humoral and cellular immune parameters in insulin-dependent diabetes mellitus type I: a long-term follow-up study*. J Endocrinol, 1989. 121(1): p. 177-83.

52. Vague, P., et al., *Effect of cyclosporin A on B-cell loss in type 1 (insulin-dependent) diabetes mellitus*. Diabetologia, 1989. 32(12): p. 887.

53. Dupre, J., et al., *Induction and pathophysiology of remission of insulin-dependent diabetes mellitus during administration of ciclosporin. London Diabetes Study Group*. Horm Res, 1990. 33(2-4): p. 152-8.

54. Snorgaard, O., S. G. Hartling, and C. Binder, *Proinsulin and C-peptide at onset and during* 12 months cyclosporin treatment of type 1 (*insulin-dependent*) *diabetes mellitus*. Diabetologia, 1990. 33(1): p. 36-42.

55. Mandrup-Poulsen, T., et al., *Lack of predictive value of islet cell antibodies, insulin antibodies, and HLA-DR phenotype for remission in cyclosporin-treated IDDM patients. The Canadian-European Randomized Control Trial Group*. Diabetes, 1990. 39(2): p. 204-10.

56. Chase, H. P., et al., *Cyclosporine A for the treatment of new-onset insulin-dependent diabetes mellitus*. Pediatrics, 1990. 85(3): p. 241-5.

57. Descamps-Latscha, B., A. T. Nguyen, and G. Feutren, *Phagocyte oxidative metabolism in cyclosporine- or placebo-treated patients with insulin-dependent* (*type I*) *diabetes mellitus of recent onset*. J Autoimmun, 1990. 3(2): p. 201-13.

58. Assan, R., et al., *Plasma C-peptide levels and clinical remissions in recent-onset type I diabetic patients treated with cyclosporin A and insulin*. Diabetes, 1990. 39(7): p. 768-74.

59. Lipton, R., et al., *Cyclosporin therapy for prevention and cure of IDDM. Epidemiological perspective of benefits and risks*. Diabetes Care, 1990. 13(7): p. 776-84.

60. Papoz, L., et al., *Probability of remission in individual in early adult insulin dependent diabetic patients. Results from the Cyclosporine Diabetes French Study Group*. Diabete Metab, 1990. 16(4): p. 303-10.

61. Vialettes, B., et al., *A preliminary multicentre study of the treatment of recently diagnosed type* 1 *diabetes by combination nicotinamide-cyclosporin therapy*. Diabet Med, 1990. 7(8): p. 731-5.

62. Atkison, P. R., et al., *Interaction of bromocriptine and cyclosporine in insulin dependent diabetes mellitus: results from the Canadian open study*. J Autoimmun, 1990. 3(6): p. 793-9.

63. Mihatsch, M. J., et al., *Kidney biopsy findings in cyclosporine-treated patients with insulin-dependent diabetes mellitus*. Klin Wochenschr, 1991. 69(8): p. 354-9.

64. Martin, S., et al., *Follow-up of cyclosporin A treatment in type* 1 (*insulin-dependent*) *diabetes mellitus: lack of long-term effects*. Diabetologia, 1991. 34(6): p. 429-34.

65. Feutren, G., G. de The, and J. F. Bach, *Epstein-Barr virus serology and isoelectrofocusing pattern of serum immunoglobulins in cyclosporin or placebo-treated type I diabetics*. J Autoimmun, 1992. 5(2): p. 161-72.

66. Skyler, J. S. and A. Rabinovitch, *Cyclosporine in recent onset type I diabetes mellitus. Effects on islet beta cell function. Miami Cyclosporine Diabetes Study Group*. J Diabetes Complications, 1992. 6(2): p. 77-88.

67. Hramiak, I. M., J. Dupre, and D. T. Finegood, *Determinants of clinical remission in recent-onset IDDM*. Diabetes Care, 1993. 16(1): p. 125-32.

68. Faulds, D., K. L. Goa, and P. Benfield, *Cyclosporin. A review of its pharmacodynamic and pharmacokinetic properties, and therapeutic use in immunoregulatory disorders*. Drugs, 1993. 45(6): p. 953-1040.

69. Mahon, J. L., J. Dupre, and C. R. Stiller, *Lessons learned from use of cyclosporine for insulin-dependent diabetes mellitus. The case for immunotherapy for insulin-dependent diabetics having residual insulin secretion*. Ann N Y Acad Sci, 1993. 696: p. 351-63.

70. Burke, G. W., et al., *Effect of cyclosporine A on serum tumor necrosis factor alpha in new-onset type I* (*insulin-dependent*) *diabetes mellitus*. J Diabetes Complications, 1994. 8(1): p. 40-4.

71. Pozzilli, P., et al., *Randomized trial comparing nicotinamide and nicotinamide plus cyclosporin in recent onset insulin-dependent diabetes* (*IMDIAB* 1). *The IMDIAB Study Group*. Diabet Med, 1994. 11(1): p. 98-104.

72. Petersen, J. S., et al., *Glutamic acid decarboxylase* (*GAD*65) *autoantibodies in prediction of beta-cell function and remission in recent-onset IDDM after cyclosporin treatment. The Canadian-European Randomized Control Trial Group*. Diabetes, 1994. 43(11): p. 1291-6.

73. Letizia, C., et al., *Serum angiotensin-converting enzyme levels in patients with recent-onset insulin-dependent diabetes after one year of low-dose cyclosporin therapy. IMDIAB Study Group*. Int J Clin Pharmacol Res, 1995. 15(5-6): p. 209-13.

74. Rakotoambinina, B., et al., *Cyclosporin A does not delay insulin dependency in asymptomatic IDDM patients*. Diabetes Care, 1995. 18(11): p. 1487-90.

75. De Filippo, G., et al., *Long-term results of early cyclosporin therapy in juvenile IDDM*. Diabetes, 1996. 45(1): p. 101-4.

76. Hannedouche, T. P., et al., *Angiotensin converting enzyme inhibition and chronic cyclosporine-induced renal dysfunction in type* 1 *diabetes*. Nephrol Dial Transplant, 1996. 11(4): p. 673-8.

77. Carel, J. C., et al., *Cyclosporine delays but does not prevent clinical onset in glucose intolerant pre-type* 1 *diabetic children*. J Autoimmun, 1996. 9(6): p. 739-45.

78. Parving, H. H., et al., *Cyclosporine nephrotoxicity in type* 1 *diabetic patients. A* 7-*year follow-up study*. Diabetes Care, 1999. 22(3): p. 478-83.

79. Christie, M. R., et al., *IA*-2 *antibody-negative status predicts remission and recovery of C-peptide levels in type* 1 *diabetic patients treated with cyclosporin*. Diabetes Care, 2002. 25(7): p. 1192-7.

80. Assan, R., et al., *Normal renal function* 8 *to* 13 *years after cyclosporin A therapy in* 285 *diabetic patients*. Diabetes Metab Res Rev, 2002. 18(6): p. 464-72.

81. Gandhi, G. Y., et al., *Immunotherapeutic agents in type* 1 *diabetes: a systematic review and meta-analysis of randomized trials*. Clin Endocrinol (Oxf), 2008. 69(2): p. 244-52.

82. Sobel, D. O., A. Henzke, and V. Abbassi, *Cyclosporin and methotrexate therapy induces remission in type* 1 *diabetes mellitus*. Acta Diabetol, 2010. 47(3): p. 243-50.

83. Harrison, L. C., et al., *Increase in remission rate in newly diagnosed type I diabetic subjects treated with azathioprine*. Diabetes, 1985. 34(12): p. 1306-8.

84. Teraoka, S., et al., *Effect of rescue therapy using FK* 506 *on relapsing rejection after combined pancreas and kidney transplantation*. Transplant Proc, 1995. 27(1): p. 1335-9.

85. Carroll, P. B., et al., *The use of FK* 506 *in new-onset type I diabetes in man*. Transplant Proc, 1991. 23(6): p. 3351-3.

86. Odorico, J. S. and H. W. Sollinger, *Technical and immunosuppressive advances in transplantation for insulin-dependent diabetes mellitus*. World J Surg, 2002. 26(2): p. 194-211.

87. Bolla, A. M., et al., *Rapamycin Plus Vildagliptin to Recover beta-Cell Function in Long-Standing Type* 1 *Diabetes: A Double-Blind, Randomized Trial*. J Clin Endocrinol Metab, 2021. 106(2): p. e507-e519.

88. Monti, P., et al., *Rapamycin monotherapy in patients with type* 1 *diabetes modifies CD*4+*CD*25+*FOXP*3+ *regulatory T-cells*. Diabetes, 2008. 57(9): p. 2341-7.

89. Piemonti, L., et al., *Beta cell function during rapamycin monotherapy in long-term type* 1 *diabetes*. Diabetologia, 2011. 54(2): p. 433-9.

90. Long, S. A., et al., *Rapamycin/IL*-2 *combination therapy in patients with type* 1 *diabetes augments Tregs yet transiently impairs beta-cell function*. Diabetes, 2012. 61(9): p. 2340-8.

91. Hirsch, R., J. D. Ellenhorn, and J. A. Bluestone, *In vivo administration of anti-CD*3 *monoclonal antibody can activate immune responses thus preventing malignant tumor growth*. Princess Takamatsu Symp, 1988. 19: p. 237-43.

92. Schoof, D. D., et al., *Activation of human tumor-infiltrating lymphocytes by monoclonal antibodies directed to the CD*3 *complex*. Cancer Res, 1990. 50(4): p. 1138-43.

93. Davis, L. S., M. C. Wacholtz, and P. E. Lipsky, *The induction of T cell unresponsiveness by rapidly modulating CD*3. J Immunol, 1989. 142(4): p. 1084-94.

94. Anasetti, C., et al., *Induction of specific nonresponsiveness in unprimed human T cells by anti-CD*3 *antibody and alloantigen*. J Exp Med, 1990. 172(6): p. 1691-700.

95. Woodle, E. S., et al., *Phase I trial of a humanized, Fc receptor nonbinding OKT*3 *antibody, huOKT*3*gamma*1 (*Ala-Ala*) *in the treatment of acute renal allograft rejection*. Transplantation, 1999. 68(5): p. 608-16.

96. Cosimi, A. B., et al., *Treatment of acute renal allograft rejection with OKT*3 *monoclonal antibody*. Transplantation, 1981. 32(6): p. 535-9.

97. Ortho Multicenter Transplant Study, G., *A randomized clinical trial of OKT*3 *monoclonal antibody for acute rejection of cadaveric renal transplants*. N Engl J Med, 1985. 313(6): p. 337-42.

98. Debure, A., et al., *One-month prophylactic use of OKT*3 *in cadaver kidney transplant recipients*. Transplantation, 1988. 45(3): p. 546-53.

99. Oh, H. K., et al., *Two low-dose OKT*3 *induction regimens following renal transplantation—clinical experience at a single center*. Clin Transplant, 1998. 12(4): p. 343-7.

100. Opelz, G., *Efficacy of rejection prophylaxis with OKT*3 *in renal transplantation*. Collaborative Transplant Study. Transplantation, 1995. 60(11): p. 1220-4.

101. Darby, C. R., et al., *Reduced dose OKT*3 *prophylaxis in sensitised kidney recipients*. Transpl Int, 1996. 9(6): p. 565-9.

102. Ciancio, G., et al., *Human donor bone marrow cells can enhance hyporeactivity in renal transplantation using maintenance FK* 506 *and OKT*3 *induction therapy*. Transplant Proc, 1996. 28(2): p. 943-4.

103. Waid, T. H., et al., *Treatment of renal allograft rejection with T*10*B*9.1*A*31 *or OKT*3: *final analysis of a phase II clinical trial*. Transplantation, 1997. 64(2): p. 274-81.

104. Kumar, M. S., et al., *ATGAM versus OKT*3 *induction therapy in cadaveric kidney transplantation: patient and graft survival, CD*3 *subset, infection, and cost analysis*. Transplant Proc, 1998. 30(4): p. 1351-2.

105. Cosimi, A. B., et al., *A randomized clinical trial comparing OKT*3 *and steroids for treatment of hepatic allograft rejection*. Transplantation, 1987. 43(1): p. 91-5.

106. Millis, J. M., et al., *Randomized prospective trial of OKT*3 *for early prophylaxis of rejection after liver transplantation*. Transplantation, 1989. 47(1): p. 82-8.

107. Whiting, J. F., et al., *Use of low-dose OKT*3 *as induction therapy in liver transplantation*. Transplantation, 1998. 65(4): p. 577-80.

108. Melzer, J. S., et al., *The use of OKT*3 *in combined pancreas-kidney allotransplantation*. Transplant Proc, 1990. 22(2): p. 634-5.

109. Sindhi, R., et al., *Increased risk of pulmonary edema in diabetic patients undergoing preemptive pancreas transplantation with OKT*3 *induction*. Transplant Proc, 1995. 27(6): p. 3016-7.

110. Stratta, R. J., et al., *A prospective randomized trial of OKT*3 *vs ATGAM induction therapy in pancreas transplant recipients*. Transplant Proc, 1996. 28(2): p. 917-8.

111. Ross, D. J., et al., *Delayed development of obliterative bronchiolitis syndrome with OKT*3 *after unilateral lung transplantation. A plea for multicenter immunosuppressive trials*. Chest, 1996. 109(4): p. 870-3.

112. van Gelder, T., et al., *A randomized trial comparing safety and efficacy of OKT*3 *and a monoclonal anti-interleukin*-2 *receptor antibody* (*BT*563) *in the prevention of acute rejection after heart transplantation*. Transplantation, 1996. 62(1): p. 51-5.

113. Delgado, J. F., et al., *Induction treatment with monoclonal antibodies for heart transplantation*. Transplant Rev (Orlando), 2011. 25(1): p. 21-6.

114. Kormos, R. L., et al., *Monoclonal versus polyclonal antibody therapy for prophylaxis against rejection after heart transplantation*. J Heart Transplant, 1990. 9(1): p. 1-9, discussion 9-10.

115. Rabinov, M., et al., *Recipient selection algorithm for immunosuppression in cardiac transplantation: OKT*3 *vs triple therapy alone*. Transplant Proc, 1992. 24(1): p. 167-8.

116. Chin, C., et al., *Induction therapy for pediatric and adult heart transplantation: comparison between OKT*3 *and daclizumab*. Transplantation, 2005. 80(4): p. 477-81.

117. Prentice, H. G., et al., *Use of anti-T-cell monoclonal antibody OKT*3 *to prevent acute graft-versus-host disease in allogeneic bone-marrow transplantation for acute leukaemia*. Lancet, 1982. 1(8274): p. 700-3.

118. Weinshenker, B. G., et al., *An open trial of OKT*3 *in patients with multiple sclerosis*. Neurology, 1991. 41(7): p. 1047-52.

119. Herold, K. C., et al., *A single course of anti-CD*3 *monoclonal antibody hOKT*3*gamma*1(*Ala-Ala*) *results in improvement in C-peptide responses and clinical parameters for at least* 2 years after onset of type 1 diabetes. Diabetes, 2005. 54(6): p. 1763-9.

120. Ferran, C., et al., *Cytokine-related syndrome following injection of anti-CD*3 *monoclonal antibody: further evidence for transient in vivo T cell activation*. Eur J Immunol, 1990. 20(3): p. 509-15.

121. Vasquez, E. M., A. J. Fabrega, and R. Pollak, *OKT*3-*induced cytokine-release syndrome: occurrence beyond the second dose and association with rejection severity*. Transplant Proc, 1995. 27(1): p. 873-4.

122. Norman, D. J., J. A. Kimball, and J. M. Barry, *Cytokine-release syndrome: differences between high and low doses of OKT*3. Transplant Proc, 1993. 25(2 Suppl 1): p. 35-8.

123. Goldman, M., et al., *OKT*3-*induced cytokine release attenuation by high-dose methylprednisolone*. Lancet, 1989. 2(8666): p. 802-3.

124. Fletcher, E. A. K., et al., *Extracorporeal human whole blood in motion, as a tool to predict first-infusion reactions and mechanism-of-action of immunotherapeutics*. Int Immunopharmacol, 2018. 54: p. 1-11.

125. Chatenoud, L., et al., *In vivo cell activation following OKT3 administration. Systemic cytokine release and modulation by corticosteroids*. Transplantation, 1990. 49(4): p. 697-702.

126. Chatenoud, L., et al., *Corticosteroid inhibition of the OKT3-induced cytokine-related syndrome—dosage and kinetics prerequisites*. Transplantation, 1991. 51(2): p. 334-8.

127. Bugelski, P. J., et al., *Monoclonal antibody-induced cytokine-release syndrome*. Expert Rev Clin Immunol, 2009. 5(5): p. 499-521.

128. Barel, D., et al., *Enhanced tumor necrosis factor in anti-CD3 antibody stimulated diabetic NOD mice: modulation by PGE1 and dietary lipid*. Autoimmunity, 1992. 13(2): p. 141-9.

129. Pradier, O., et al., *Procoagulant effect of the OKT3 monoclonal antibody: involvement of tumor necrosis factor*. Kidney Int, 1992. 42(5): p. 1124-9.

130. Wissing, K. M., et al., *A pilot trial of recombinant human interleukin-10 in kidney transplant recipients receiving OKT3 induction therapy*. Transplantation, 1997. 64(7): p. 999-1006.

131. Charpentier, B., et al., *Evidence that antihuman tumor necrosis factor monoclonal antibody prevents OKT3-induced acute syndrome*. Transplantation, 1992. 54(6): p. 997-1002.

132. DeVault, G. A., Jr., et al., *The effects of oral pentoxifylline on the cytokine release syndrome during inductive OKT3*. Transplantation, 1994. 57(4): p. 532-40.

133. Ilan, Y., et al., *Oral administration of OKT3 monoclonal antibody to human subjects induces a dose-dependent immunologic effect in T cells and dendritic cells*. J Clin Immunol, 2010. 30(1): p. 167-77.

134. Lalazar, G., et al., *Oral Administration of OKT3 MAb to Patients with NASH, Promotes Regulatory T-cell Induction, and Alleviates Insulin Resistance: Results of a Phase IIa Blinded Placebo-Controlled Trial*. J Clin Immunol, 2015. 35(4): p. 399-407.

135. Gale, E. A., *Theory and practice of nicotinamide trials in pre-type 1 diabetes*. J Pediatr Endocrinol Metab, 1996. 9(3): p. 375-9.

136. Holstad, M., L. Jansson, and S. Sandler, *Inhibition of nitric oxide formation by aminoguanidine: an attempt to prevent insulin-dependent diabetes mellitus*. Gen Pharmacol, 1997. 29(5): p. 697-700.

137. Bonner-Weir, S., et al., *The pancreatic ductal epithelium serves as a potential pool of progenitor cells*. Pediatr Diabetes, 2004. 5 Suppl 2: p. 16-22.

138. Bonner-Weir, S., et al., *A second pathway for regeneration of adult exocrine and endocrine pancreas. A possible recapitulation of embryonic development*. Diabetes, 1993. 42(12): p. 1715-20.

139. Rosenberg, L., *In vivo cell transformation: neogenesis of beta cells from pancreatic ductal cells*. Cell Transplant, 1995. 4(4): p. 371-83.

140. Jindal, R. M., et al., *Proliferation of rat pancreatic ductal-epithelial cells in vitro, and in response to partial hepatectomy and pancreatectomy in vivo*. Transplant Proc, 1995. 27(6): p. 2991-2.

141. Jindal, R. M., et al., *Stem cell potential of pancreatic ductal-epithelial cells*. Transplant Proc, 1997. 29(1-2): p. 1502-4.

142. Song, S. Y., et al., *Expansion of Pdx1-expressing pancreatic epithelium and islet neogenesis in transgenic mice overexpressing transforming growth factor alpha*. Gastroenterology, 1999. 117(6): p. 1416-26.

143. Maldonado, T. S., et al., *Basement membrane exposure defines a critical window of competence for pancreatic duct differentiation from undifferentiated pancreatic precursor cells*. Pancreas, 2000. 21(1): p. 93-6.

144. Cirulli, V., et al., *Expression and function of alpha(v) beta(3) and alpha(v)beta(5) integrins in the developing pancreas: roles in the adhesion and migration of putative endocrine progenitor cells*. J Cell Biol, 2000. 150(6): p. 1445-60.

145. Taguchi, M., T. Yamaguchi, and M. Otsuki, *Induction of PDX-1-positive cells in the main duct during regeneration after acute necrotizing pancreatitis in rats*. J Pathol, 2002. 197(5): p. 638-46.

146. Okumura, K., et al., *Salivary gland progenitor cells induced by duct ligation differentiate into hepatic and pancreatic lineages*. Hepatology, 2003. 38(1): p. 104-13.

147. Gatto, C., et al., *Effects of cryopreservation and coculture with pancreatic ductal epithelial cells on insulin secretion from human pancreatic islets*. Int J Mol Med, 2003. 12(6): p. 851-4.

148. Kayali, A. G., et al., *The stromal cell-derived factor-1alpha/CXCR4 ligand-receptor axis is critical for progenitor survival and migration in the pancreas*. J Cell Biol, 2003. 163(4): p. 859-69.

149. Grapin-Botton, A., *Ductal cells of the pancreas*. Int J Biochem Cell Biol, 2005. 37(3): p. 504-10.

150. Liu, T., et al., *PDX-1 expression in pancreatic ductal cells after partial pancreatectomy in adult rats*. J Huazhong Univ Sci Technolog Med Sci, 2004. 24(5): p. 464-6.

151. Peters, K., et al., *Expression of stem cell markers and transcription factors during the remodeling of the rat pancreas after duct ligation*. Virchows Arch, 2005. 446 (1): p. 56-63.

152. Oshima, Y., et al., *Isolation of mouse pancreatic ductal progenitor cells expressing CD133 and c-Met by flow cytometric cell sorting*. Gastroenterology, 2007. 132(2): p. 720-32.

153. Lynn, F. C., et al., *Sox9 coordinates a transcriptional network in pancreatic progenitor cells*. Proc Natl Acad Sci USA, 2007. 104(25): p. 10500-5.

154. Chen, B., et al., *Would pancreas duct-epithelium-derived stem/progenitor cells enhance islet allograft survival by means of islets recruitment and tolerance induction in Edmonton protocol era?* Med Hypotheses, 2008. 70(3): p. 661-4.

155. Bonner-Weir, S., et al., *Transdifferentiation of pancreatic ductal cells to endocrine beta-cells*. Biochem Soc Trans, 2008. 36(Pt 3): p. 353-6.

156. Xia, B., et al., *Can pancreatic duct-derived progenitors be a source of islet regeneration?* Biochem Biophys Res Commun, 2009. 383(4): p. 383-5.

157. May, R., et al., *Identification of a novel putative pancreatic stem/progenitor cell marker DCAMKL-1 in normal mouse pancreas*. Am J Physiol Gastrointest Liver Physiol, 2010. 299(2): p. G303-10.

158. Li, W. C., et al., *Activation of pancreatic-duct-derived progenitor cells during pancreas regeneration in adult rats*. J Cell Sci, 2010. 123(Pt 16): p. 2792-802.

159. Lysy, P. A., G. C. Weir, and S. Bonner-Weir, *Making beta cells from adult cells within the pancreas*. Curr Diab Rep, 2013. 13(5): p. 695-703.

160. Yamaguchi, J., et al., *Pancreatic duct glands (PDGs) are a progenitor compartment responsible for pancreatic ductal epithelial repair*. Stem Cell Res, 2015. 15(1): p. 190-202.

161. Marty-Santos, L. and O. Cleaver, *Progenitor Epithelium: Sorting Out Pancreatic Lineages*. J Histochem Cytochem, 2015. 63(8): p. 559-74.

162. Carpino, G., et al., *iProgenitor cell niches in the human pancreatic duct system and associated pancreatic duct glands: an anatomical and immunophenotyping study*. J Anat, 2016. 228(3): p. 474-86.

163. Manda, J. K., B. J. Page, and V. Tchokonte-Nana, *Mesenchymal cells are required for epithelial duct cell-to-beta cell maturation and function in an injured adult pancreas in the rat*. Acta Histochem, 2017. 119(7): p. 689-695.

164. Wang, X., et al., *Formation of pancreatic duct epithelium from bone marrow during neonatal development*. Stem Cells, 2006. 24(2): p. 307-14.

165. Marrache, F., et al., *Role of bone marrow-derived cells in experimental chronic pancreatitis*. Gut, 2008. 57(8): p. 1113-20.

166. Bell, G. I., et al., *Transplanted human bone marrow progenitor subtypes stimulate endogenous islet regeneration and revascularization*. Stem Cells Dev, 2012. 21(1): p. 97-109.

167. Bell, G. I., et al., *Combinatorial human progenitor cell transplantation optimizes islet regeneration through secretion of paracrine factors*. Stem Cells Dev, 2012. 21(11): p. 1863-76.

168. Pittenger, G. L., A. I. Vinik, and L. Rosenberg, *The partial isolation and characterization of ilotropin, a novel islet-specific growth factor*. Adv Exp Med Biol, 1992. 321: p. 123-30; discussion 131-2.

169. Nielsen, J. H., et al., *The role of growth hormone and prolactin in beta cell growth and regeneration*. Adv Exp Med Biol, 1992. 321: p. 9-17; discussion 19-20.

170. Movassat, J., C. Saulnier, and B. Portha, *Insulin administration enhances growth of the beta-cell mass in streptozotocin-treated newborn rats*. Diabetes, 1997. 46(9): p. 1445-52.

171. Holstad, M. and S. Sandler, *Prolactin protects against diabetes induced by multiple low doses of streptozotocin in mice*. J Endocrinol, 1999. 163(2): p. 229-34.

172. Xu, G., et al., *Exendin-4 stimulates both beta-cell replication and neogenesis, resulting in increased beta-cell mass and improved glucose tolerance in diabetic rats*. Diabetes, 1999. 48(12): p. 2270-6.

173. Cui, H., et al., *Safety, Pharmacokinetics and Pharmacodynamics of Multiple Escalating Doses of PEGylated Exenatide (PB-119) in Healthy Volunteers*. Eur J Drug Metab Pharmacokinet, 2021. 46(2): p. 265-275.

174. Song, X., et al., *Combined Treatment with Bone Marrow-Derived Mesenchymal Stem Cells and Exendin-4 Promotes Islet Regeneration in Streptozotocin-Induced Diabetic Rats*. Stem Cells Dev, 2021. 30(9): p. 502-514.

175. Tourrel, C., et al., *Glucagon-like peptide-1 and exendin-4 stimulate beta-cell neogenesis in streptozotocin-treated newborn rats resulting in persistently improved glucose homeostasis at adult age*. Diabetes, 2001. 50(7): p. 1562-70.

176. Bakbak, E., et al., *Lessons from bariatric surgery: Can increased GLP-1 enhance vascular repair during cardiometabolic-based chronic disease?* Rev Endocr Metab Disord, 2021.

177. Abdulmalik, S., et al., *The glucagon-like peptide 1 receptor agonist Exendin-4 induces tenogenesis in human mesenchymal stem cells*. Differentiation, 2021. 120: p. 1-9.

178. Mehta, K., et al., *Deciphering the Neuroprotective Role of Glucagon-like Peptide-1 Agonists in Diabetic Neuropathy: Current Perspective and Future Directions*. Curr Protein Pept Sci, 2021. 22(1): p. 4-18.

179. Villalba, A., et al., *Repurposed Analog of GLP-1 Ameliorates Hyperglycemia in Type 1 Diabetic Mice Through Pancreatic Cell Reprogramming*. Front Endocrinol (Lausanne), 2020. 11: p. 258.

180. Wei, R., et al., *Dapagliflozin promotes beta cell regeneration by inducing pancreatic endocrine cell phenotype conversion in type 2 diabetic mice*. Metabolism, 2020. 111: p. 154324.

181. Li, L., et al., *Promotion of beta-cell regeneration by betacellulin in ninety percent-pancreatectomized rats*. Endocrinology, 2001. 142(12): p. 5379-85.

182. Li, L., et al., *Betacellulin improves glucose metabolism by promoting conversion of intraislet precursor cells to beta-cells in streptozotocin-treated mice*. Am J Physiol Endocrinol Metab, 2003. 285(3): p. E577-83.

183. Lee, Y. S., G. J. Song, and H. S. Jun, *Betacellulin-Induced alpha-Cell Proliferation Is Mediated by ErbB3 and ErbB4, and May Contribute to beta-Cell Regeneration*. Front Cell Dev Biol, 2020. 8: p. 605110.

184. Li, L., et al., *Activin A and betacellulin: effect on regeneration of pancreatic beta-cells in neonatal streptozotocin-treated rats*. Diabetes, 2004. 53(3): p. 608-15.

185. Rooman, I., J. Lardon, and L. Bouwens, *Gastrin stimulates beta-cell neogenesis and increases islet mass from transdifferentiated but not from normal exocrine pancreas tissue*. Diabetes, 2002. 51(3): p. 686-90.

186. Rooman, I. and L. Bouwens, *Combined gastrin and epidermal growth factor treatment induces islet regeneration and restores normoglycaemia in C57B16/J mice treated with alloxan*. Diabetologia, 2004. 47(2): p. 259-65.

187. George, M., et al., *Beta cell expression of IGF-I leads to recovery from type 1 diabetes*. J Clin Invest, 2002. 109(9): p. 1153-63.

188. Agudo, J., et al., *IGF-I mediates regeneration of endocrine pancreas by increasing beta cell replication through cell cycle protein modulation in mice*. Diabetologia, 2008. 51(10): p. 1862-72.

189. Sharma, A., et al., *The homeodomain protein IDX-1 increases after an early burst of proliferation during pancreatic regeneration*. Diabetes, 1999. 48(3): p. 507-13.

190. Watanabe, T., et al., *Pancreatic beta-cell replication and amelioration of surgical diabetes by Reg protein*. Proc Natl Acad Sci USA, 1994. 91(9): p. 3589-92.

191. Okamoto, H., *The Reg gene family and Reg proteins: with special attention to the regeneration of pancreatic beta-cells*. J Hepatobiliary Pancreat Surg, 1999. 6(3): p. 254-62.

192. Kobayashi, S., et al., *Identification of a receptor for reg (regenerating gene) protein, a pancreatic beta-cell regeneration factor*. J Biol Chem, 2000. 275(15): p. 10723-6.

193. Kodama, M., et al., *Embryonic stem cell transplantation correlates with endogenous neurogenin 3 expression and pancreas regeneration in streptozotocin-injured mice*. J Histochem Cytochem, 2009. 57(12): p. 1149-58.

194. Magenheim, J., et al., *Ngn3(+) endocrine progenitor cells control the fate and morphogenesis of pancreatic ductal epithelium*. Dev Biol, 2011. 359(1): p. 26-36.

195. Jiang, F. X. and G. Morahan, *Pancreatic stem cells: from possible to probable*. Stem Cell Rev Rep, 2012. 8(3): p. 647-57.

196. Gribben, C., et al., *Ductal Ngn3-expressing progenitors contribute to adult beta cell neogenesis in the pancreas*. Cell Stem Cell, 2021.

197. Zbinden, A., et al., *Nidogen-1 Mitigates Ischemia and Promotes Tissue Survival and Regeneration*. Adv Sci (Weinh), 2021. 8(4): p. 2002500.

198. Zhang, H., et al., *Multiple, temporal-specific roles for HNF6 in pancreatic endocrine and ductal differentiation*. Mech Dev, 2009. 126(11-12): p. 958-73.

199. Rezanejad, H., et al., *Heterogeneity of SOX9 and HNF1beta in Pancreatic Ducts Is Dynamic*. Stem Cell Reports, 2018. 10(3): p. 725-738.

200. Takahashi, I., et al., *Important role of heparan sulfate in postnatal islet growth and insulin secretion*. Biochem Biophys Res Commun, 2009. 383(1): p. 113-8.

201. Sachs, S., et al., *Targeted pharmacological therapy restores beta-cell function for diabetes remission*. Nat Metab, 2020. 2(2): p. 192-209.

202. Pittenger, G. L., D. Taylor-Fishwick, and A. I. Vinik, *The role of islet neogeneis-associated protein (INGAP) in pancreatic islet neogenesis*. Curr Protein Pept Sci, 2009. 10(1): p. 37-45.

203. Kapur, R., et al., *Short-term effects of INGAP and Reg family peptides on the appearance of small beta-cells clusters in non-diabetic mice*. Islets, 2012. 4(1): p. 40-8.

204. Kerem, M., et al., *Exogenous ghrelin enhances endocrine and exocrine regeneration in pancreatectomized rats*. J Gastrointest Surg, 2009. 13(4): p. 775-83.

205. Kayali, A. G., et al., *The SDF-1alpha/CXCR4 axis is required for proliferation and maturation of human fetal pancreatic endocrine progenitor cells*. PLoS One, 2012. 7(6): p. e38721.

206. Koya, V., et al., *Reversal of streptozotocin-induced diabetes in mice by cellular transduction with recombinant pancreatic transcription factor pancreatic duodenal homeobox-1: a novel protein transduction domain-based therapy*. Diabetes, 2008. 57(3): p. 757-69.

207. Luo, L., J. Z. Luo, and I. M. Jackson, T*hyrotropin-releasing hormone (TRH) reverses hyperglycemia in rat*. Biochem Biophys Res Commun, 2008. 374(1): p. 69-73.

208. Shanmugasundaram, E. R., et al., *Possible regeneration of the islets of Langerhans in streptozotocin-diabetic rats given Gymnema sylvestre leaf extracts*. J Ethnopharmacol, 1990. 30(3): p. 265-79.

209. Kanter, M., et al., *Partial regeneration/proliferation of the beta-cells in the islets of Langerhans by Nigella sativa L. in streptozotocin-induced diabetic rats*. Tohoku J Exp Med, 2003. 201(4): p. 213-9.

210. Takatori, A., et al., *Protective effects of probucol treatment on pancreatic beta-cell function of SZ-induced diabetic APA hamsters*. Exp Anim, 2003. 52(4): p. 317-27.

211. Li, R. J., et al., [*Effect of Astragalus polysaccharide on pancreatic cell mass in type 1 diabetic mice*]. Zhongguo Zhong Yao Za Zhi, 2007. 32(20): p. 2169-73.

212. Singh, N. and M. Gupta, *Regeneration of beta cells in islets of Langerhans of pancreas of alloxan diabetic rats by acetone extract of Momordica charantia (Linn.) (bitter gourd) fruits*. Indian J Exp Biol, 2007. 45(12): p. 1055-62.

213. Mziaut, H., et al., *ICA512 signaling enhances pancreatic beta-cell proliferation by regulating cyclins D through STATs*. Proc Natl Acad Sci USA, 2008. 105(2): p. 674-9.

214. Ansarullah, et al., *Oreocnide integrifolia Flavonoids Augment Reprogramming for Islet Neogenesis and beta-Cell Regeneration in Pancreatectomized BALB/c Mice*. Evid Based Complement Alternat Med, 2012. 2012: p. 260467.

215. Wang, Y., et al., *Agaricus bisporus lectins mediates islet beta-cell proliferation through regulation of cell cycle proteins*. Exp Biol Med (Maywood), 2012. 237(3): p. 287-96.

216. Wang, Y., et al., *Antihyperglycemic effect of ginsenoside Rh2 by inducing islet beta-cell regeneration in mice*. Horm Metab Res, 2012. 44(1): p. 33-40.

217. Zhao, Z., et al., *FTY720 normalizes hyperglycemia by stimulating beta-cell in vivo regeneration in db/db mice through regulation of cyclin D3 and p57(KIP2)*. J Biol Chem, 2012. 287(8): p. 5562-73.

218. Arora, S. K., et al., *Evaluation of pancreatic regeneration activity of Tephrosia purpurea leaves in rats with streptozotocin-induced diabetes*. J Tradit Complement Med, 2021. 11(5): p. 435-445.

219. Tootee, A., et al., *Assessment of immune-alternations and their correlations with therapeutic outcomes of transplantation of autologous Mesenchymal and Allogenic fetal stem cells in patients with type 1 diabetes: a study protocol*. J Diabetes Metab Disord, 2021. 20(1): p. 1067-1073.

220. Lu, J., et al., *One repeated transplantation of allogeneic umbilical cord mesenchymal stromal cells in type 1 diabetes: an open parallel controlled clinical study*. Stem Cell Res Ther, 2021. 12(1): p. 340.

221. Nestle, F. O., et al., *Vaccination of melanoma patients with peptide- or tumor lysate-pulsed dendritic cells*. Nat Med, 1998. 4(3): p. 328-32.

222. Chakraborty, N. G., et al., *Immunization with a tumor-cell-lysate-loaded autologous-antigen-presenting-cell-based vaccine in melanoma*. Cancer Immunol Immunother, 1998. 47(1): p. 58-64.

223. Wang, F., et al., *Phase I trial of a MART-1 peptide vaccine with incomplete Freund's adjuvant for resected high-risk melanoma*. Clin Cancer Res, 1999. 5(10): p. 2756-65.

224. Thurner, B., et al., *Vaccination with mage-3A1 peptide-pulsed mature, monocyte-derived dendritic cells expands specific cytotoxic T cells and induces regression of some metastases in advanced stage IV melanoma*. J Exp Med, 1999. 190(11): p. 1669-78.

225. Thomas, R., et al., *Immature human monocyte-derived dendritic cells migrate rapidly to draining lymph nodes after intradermal injection for melanoma immunotherapy*. Melanoma Res, 1999. 9(5): p. 474-81.

226. Mackensen, A., et al., *Phase I study in melanoma patients of a vaccine with peptide-pulsed dendritic cells generated in vitro from CD34(+) hematopoietic progenitor cells*. Int J Cancer, 2000. 86(3): p. 385-92.

227. Panelli, M. C., et al., *Phase 1 study in patients with metastatic melanoma of immunization with dendritic cells presenting epitopes derived from the melanoma-associated antigens MART-1 and gp100*. J Immunother, 2000. 23(4): p. 487-98.

228. Schuler-Thurner, B., et al., *Mage-3 and influenza-matrix peptide-specific cytotoxic T cells are inducible in terminal stage HLA-A2.1+ melanoma patients by mature monocyte-derived dendritic cells*. J Immunol, 2000. 165 (6): p. 3492-6.

229. Lau, R., et al., *Phase I trial of intravenous peptide-pulsed dendritic cells in patients with metastatic melanoma*. J Immunother, 2001. 24(1): p. 66-78.

230. Banchereau, J., et al., *Immune and clinical responses in patients with metastatic melanoma to CD34(+) progenitor-derived dendritic cell vaccine*. Cancer Res, 2001. 61(17): p. 6451-8.

231. Schuler-Thurner, B., et al., *Rapid induction of tumor-specific type 1 T helper cells in metastatic melanoma patients by vaccination with mature, cryopreserved, peptide-loaded monocyte-derived dendritic cells*. J Exp Med, 2002. 195(10): p. 1279-88.

232. Palucka, A. K., et al., *Single injection of CD34+ progenitor-derived dendritic cell vaccine can lead to induction of T-cell immunity in patients with stage IV melanoma*. J Immunother, 2003. 26(5): p. 432-9.

233. Bedrosian, I., et al., *Intranodal administration of peptide pulsed mature dendritic cell vaccines results in superior CD8+ T-cell function in melanoma patients*. J Clin Oncol, 2003. 21(20): p. 3826-35.

234. Slingluff, C. L., Jr., et al., *Clinical and immunologic results of a randomized phase II trial of vaccination using four melanoma peptides either administered in granulocyte-macrophage colony-stimulating factor in adjuvant or pulsed on dendritic cells*. J Clin Oncol, 2003. 21(21): p. 4016-26.

235. Hersey, P., et al., *Phase I/II study of treatment with dendritic cell vaccines in patients with disseminated melanoma*. Cancer Immunol Immunother, 2004. 53(2): p. 125-34.

236. Vilella, R., et al., *Pilot study of treatment of biochemotherapy-refractory stage IV melanoma patients with autologous dendritic cells pulsed with a heterologous melanoma cell line lysate*. Cancer Immunol Immunother, 2004. 53(7): p. 651-8.

237. Palucka, A. K., et al., *Spontaneous proliferation and type 2 cytokine secretion by CD4+T cells in patients with metastatic melanoma vaccinated with antigen-pulsed dendritic cells*. J Clin Immunol, 2005. 25(3): p. 288-95.

238. Banchereau, J., et al., *Immune and clinical outcomes in patients with stage IV melanoma vaccinated with peptide-pulsed dendritic cells derived from CD34+ progenitors and activated with type I interferon*. J Immunother, 2005. 28(5): p. 505-16.

239. Trakatelli, M., et al., *A new dendritic cell vaccine generated with interleukin-3 and interferon-beta induces CD8+ T cell responses against NA17-A2 tumor peptide in melanoma patients*. Cancer Immunol Immunother, 2006. 55(4): p. 469-74.

240. Salcedo, M., et al., *Vaccination of melanoma patients using dendritic cells loaded with an allogeneic tumor cell lysate*. Cancer Immunol Immunother, 2006. 55(7): p. 819-29.

241. Linette, G. P., et al., *Immunization using autologous dendritic cells pulsed with the melanoma-associated antigen gp100-derived G280-9V peptide elicits CD8+ immunity*. Clin Cancer Res, 2005. 11(21): p. 7692-9.

242. Escobar, A., et al., *Dendritic cell immunizations alone or combined with low doses of interleukin-2 induce specific immune responses in melanoma patients*. Clin Exp Immunol, 2005. 142(3): p. 555-68.

243. Tuettenberg, A., et al., *Induction of strong and persistent MelanA/MART-1-specific immune responses by adjuvant dendritic cell-based vaccination of stage II melanoma patients*. Int J Cancer, 2006. 118(10): p. 2617-27.

244. Schadendorf, D., et al., *Dacarbazine (DTIC) versus vaccination with autologous peptide-pulsed dendritic cells (DC) in first-line treatment of patients with metastatic melanoma: a randomized phase III trial of the DC study group of the DeCOG*. Ann Oncol, 2006. 17(4): p. 563-70.

245. Di Pucchio, T., et al., *Immunization of stage IV melanoma patients with Melan-A/MART-1 and gp100 peptides plus IFN-alpha results in the activation of specific CD8(+) T cells and monocyte/dendritic cell precursors*. Cancer Res, 2006. 66(9): p. 4943-51.

246. Nakai, N., et al., *Vaccination of Japanese patients with advanced melanoma with peptide, tumor lysate or both peptide and tumor lysate pulsed mature, monocyte-derived dendritic cells*. J Dermatol, 2006. 33(7): p. 462-72.

247. Palucka, A. K., et al., *Dendritic cells loaded with killed allogeneic melanoma cells can induce objective clinical responses and MART-1 specific CD8+ T-cell immunity*. J Immunother, 2006. 29(5): p. 545-57.

248. Lesimple, T., et al., *Immunologic and clinical effects of injecting mature peptide-loaded dendritic cells by intralymphatic and intranodal routes in metastatic melanoma patients*. Clin Cancer Res, 2006. 12(24): p. 7380-8.

249. Guo, J., et al., *Intratumoral injection of dendritic cells in combination with local hyperthermia induces systemic antitumor effect in patients with advanced melanoma*. Int J Cancer, 2007. 120(11): p. 2418-25.

250. O'Rourke, M. G., et al., *Dendritic cell immunotherapy for stage IV melanoma*. Melanoma Res, 2007. 17(5): p. 316-22.

251. Bercovici, N., et al., *Analysis and characterization of antitumor T-cell response after administration of dendritic cells loaded with allogeneic tumor lysate to metastatic melanoma patients*. J Immunother, 2008. 31(1): p. 101-12.

252. Hersey, P., et al., *Phase I/II study of treatment with matured dendritic cells with or without low dose IL-2 in patients with disseminated melanoma*. Cancer Immunol Immunother, 2008. 57(7): p. 1039-51.

253. von Euw, E. M., et al., *A phase I clinical study of vaccination of melanoma patients with dendritic cells loaded with allogeneic apoptotic/necrotic melanoma cells. Analysis of toxicity and immune response to the vaccine and of IL-10-1082 promoter genotype as predictor of disease progression*. J Transl Med, 2008. 6: p. 6.

254. Carrasco, J., et al., *Vaccination of a melanoma patient with mature dendritic cells pulsed with MAGE-3 peptides triggers the activity of nonvaccine anti-tumor cells*. J Immunol, 2008. 180(5): p. 3585-93.

255. Redman, B. G., et al., *Phase Ib trial assessing autologous, tumor-pulsed dendritic cells as a vaccine administered with or without IL-2 in patients with metastatic melanoma*. J Immunother, 2008. 31(6): p. 591-8.

256. Daud, A. I., et al., *Phenotypic and functional analysis of dendritic cells and clinical outcome in patients with high-risk melanoma treated with adjuvant granulocyte macrophage colony-stimulating factor*. J Clin Oncol, 2008. 26(19): p. 3235-41.

257. Engell-Noerregaard, L., et al., *Review of clinical studies on dendritic cell-based vaccination of patients with malignant melanoma: assessment of correlation between clinical response and vaccine parameters*. Cancer Immunol Immunother, 2009. 58(1): p. 1-14.

258. Nakai, N., et al., *Immunohistological analysis of peptide-induced delayed-type hypersensitivity in advanced melanoma patients treated with melanoma antigen-pulsed mature monocyte-derived dendritic cell vaccination*. J Dermatol Sci, 2009. 53(1): p. 40-7.

259. Dillman, R. O., et al., *Phase II trial of dendritic cells loaded with antigens from self-renewing, proliferating autologous tumor cells as patient-specific antitumor vaccines in patients with metastatic melanoma: final report*. Cancer Biother Radiopharm, 2009. 24(3): p. 311-9.

260. Chang, J. W., et al., *Immunotherapy with dendritic cells pulsed by autologous dactinomycin-induced melanoma*

*apoptotic bodies for patients with malignant melanoma*. Melanoma Res, 2009. 19(5): p. 309-15.

261. Trepiakas, R., et al., *Vaccination with autologous dendritic cells pulsed with multiple tumor antigens for treatment of patients with malignant melanoma: results from a phase I/II trial*. Cytotherapy, 2010. 12(6): p. 721-34.

262. Jacobs, J. F., et al., *Dendritic cell vaccination in combination with anti-CD25 monoclonal antibody treatment: a phase I/II study in metastatic melanoma patients*. Clin Cancer Res, 2010. 16(20): p. 5067-78.

263. Ribas, A., et al., *Multicenter phase II study of matured dendritic cells pulsed with melanoma cell line lysates in patients with advanced melanoma*. J Transl Med, 2010. 8: p. 89.

264. Ridolfi, L., et al., *Unexpected high response rate to traditional therapy after dendritic cell-based vaccine in advanced melanoma: update of clinical outcome and subgroup analysis*. Clin Dev Immunol, 2010. 2010: p. 504979.

265. Cornforth, A. N., et al., *Resistance to the proapoptotic effects of interferon-gamma on melanoma cells used in patient-specific dendritic cell immunotherapy is associated with improved overall survival*. Cancer Immunol Immunother, 2011. 60(1): p. 123-31.

266. Lesterhuis, W. J., et al., *Wild-type and modified gp100 peptide-pulsed dendritic cell vaccination of advanced melanoma patients can lead to long-term clinical responses independent of the peptide used*. Cancer Immunol Immunother, 2011. 60(2): p. 249-60.

267. Bjoern, J., et al., *Changes in peripheral blood level of regulatory T cells in patients with malignant melanoma during treatment with dendritic cell vaccination and low-dose IL-2*. Scand J Immunol, 2011. 73(3): p. 222-33.

268. Steele, J. C., et al., *Phase I/II trial of a dendritic cell vaccine transfected with DNA encoding melan A and gp100 for patients with metastatic melanoma*. Gene Ther, 2011. 18(6): p. 584-93.

269. Kim, D. S., et al., *Immunotherapy of malignant melanoma with tumor lysate-pulsed autologous monocyte-derived dendritic cells*. Yonsei Med J, 2011. 52(6): p. 990-8.

270. Ellebaek, E., et al., *Metastatic melanoma patients treated with dendritic cell vaccination, Interleukin-2 and metronomic cyclophosphamide: results from a phase II trial*. Cancer Immunol Immunother, 2012. 61(10): p. 1791-804.

271. Dillman, R. O., et al., *Tumor stem cell antigens as consolidative active specific immunotherapy: a randomized phase II trial of dendritic cells versus tumor cells in patients with metastatic melanoma*. J Immunother, 2012. 35(8): p. 641-9.

272. Dannull, J., et al., *Melanoma immunotherapy using mature DCs expressing the constitutive proteasome*. J Clin Invest, 2013. 123(7): p. 3135-45.

273. Finkelstein, S. E., et al., *Combination of external beam radiotherapy (EBRT) with intratumoral injection of dendritic cells as neo-adjuvant treatment of high-risk soft tissue sarcoma patients*. Int J Radiat Oncol Biol Phys, 2012. 82(2): p. 924-32.

274. Stift, A., et al., *Dendritic cell vaccination in medullary thyroid carcinoma*. Clin Cancer Res, 2004. 10(9): p. 2944-53.

275. Kuwabara, K., et al., *Results of a phase I clinical study using dendritic cell vaccinations for thyroid cancer*. Thyroid, 2007. 17(1): p. 53-8.

276. Bachleitner-Hofmann, T., et al., *Pilot trial of autologous dendritic cells loaded with tumor lysate(s) from allogeneic tumor cell lines in patients with metastatic medullary thyroid carcinoma*. Oncol Rep, 2009. 21(6): p. 1585-92.

277. Yu, J. S., et al., *Vaccination of malignant glioma patients with peptide pulsed dendritic cells elicits systemic cytotoxicity and intracranial T-cell infiltration*. Cancer Res, 2001. 61(3): p. 842-7.

278. Yamanaka, R., et al., *Vaccination of recurrent glioma patients with tumour lysate-pulsed dendritic cells elicits immune responses: results of a clinical phase I/II trial*. Br J Cancer, 2003. 89(7): p. 1172-9.

279. Yu, J. S., et al., *Vaccination with tumor lysate-pulsed dendritic cells elicits antigen-specific, cytotoxic T-cells in patients with malignant glioma*. Cancer Res, 2004. 64(14): p. 4973-9.

280. Yamanaka, R., et al., *Tumor lysate and IL-18 loaded dendritic cells elicits Th1 response, tumor-specific CD8+ cytotoxic T cells in patients with malignant glioma*. J Neurooncol, 2005. 72(2): p. 107-13.

281. Yamanaka, R., et al., *Clinical evaluation of dendritic cell vaccination for patients with recurrent glioma: results of a clinical phase I/II trial*. Clin Cancer Res, 2005. 11(11): p. 4160-7.

282. Liau, L. M., et al., *Dendritic cell vaccination in glioblastoma patients induces systemic and intracranial T-cell responses modulated by the local central nervous system tumor microenvironment*. Clin Cancer Res, 2005. 11(15): p. 5515-25.

283. Walker, D. G., et al., *Results of a phase I dendritic cell vaccine trial for malignant astrocytoma: potential interaction with adjuvant chemotherapy*. J Clin Neurosci, 2008. 15(2): p. 114-21.

284. Leplina, O. Y., et al., *Use of interferon-alpha-induced dendritic cells in the therapy of patients with malignant brain gliomas*. Bull Exp Biol Med, 2007. 143(4): p. 528-34.

285. De Vleeschouwer, S., et al., *Postoperative adjuvant dendritic cell-based immunotherapy in patients with relapsed glioblastoma multiforme*. Clin Cancer Res, 2008. 14(10): p. 3098-104.

286. Ardon, H., et al., *Adjuvant dendritic cell-based tumour vaccination for children with malignant brain tumours*. Pediatr Blood Cancer, 2010. 54(4): p. 519-25.

287. Prins, R. M., et al., *Gene expression profile correlates with T-cell infiltration and relative survival in glioblastoma patients vaccinated with dendritic cell immunotherapy*. Clin Cancer Res, 2011. 17(6): p. 1603-15.

288. Okada, H., et al., *Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma*. J Clin Oncol, 2011. 29(3): p. 330-6.

289. Fadul, C. E., et al., *Immune response in patients with newly diagnosed glioblastoma multiforme treated with intranodal autologous tumor lysate-dendritic cell vaccination after radiation chemotherapy*. J Immunother, 2011. 34(4): p. 382-9.

290. Chang, C. N., et al., *A phase I/II clinical trial investigating the adverse and therapeutic effects of a postoperative autologous dendritic cell tumor vaccine in patients with malignant glioma*. J Clin Neurosci, 2011. 18(8): p. 1048-54.

291. Cho, D. Y., et al., *Adjuvant immunotherapy with whole-cell lysate dendritic cells vaccine for glioblastoma multiforme: a phase II clinical trial*. World Neurosurg, 2012. 77(5-6): p. 736-44.

292. Iwami, K., et al., *Peptide-pulsed dendritic cell vaccination targeting interleukin-13 receptor alpha2 chain in recurrent malignant glioma patients with HLA-A*24/A*02 allele*. Cytotherapy, 2012. 14(6): p. 733-42.

293. Fong, B., et al., *Monitoring of regulatory T cell frequencies and expression of CTLA-4 on T cells, before and after DC vaccination, can predict survival in GBM patients*. PLoS One, 2012. 7(4): p. e32614.

294. De Vleeschouwer, S., et al., *Stratification according to HGG-IMMUNO RPA model predicts outcome in a large group of patients with relapsed malignant glioma treated by adjuvant postoperative dendritic cell vaccination*. Cancer Immunol Immunother, 2012. 61(11): p. 2105-12.

295. Phuphanich, S., et al., *Phase I trial of a multi-epitope-pulsed dendritic cell vaccine for patients with newly diagnosed glioblastoma*. Cancer Immunol Immunother, 2013. 62(1): p. 125-35.

296. Akiyama, Y., et al., *alpha-type-1 polarized dendritic cell-based vaccination in recurrent high-grade glioma: a phase I clinical trial*. BMC Cancer, 2012. 12: p. 623.

297. Prins, R. M., et al., *Comparison of glioma-associated antigen peptide-loaded versus autologous tumor lysate-loaded dendritic cell vaccination in malignant glioma patients*. J Immunother, 2013. 36(2): p. 152-7.

298. Shah, A. H., et al., *Dendritic cell vaccine for recurrent high-grade gliomas in pediatric and adult subjects: clinical trial protocol*. Neurosurgery, 2013. 73(5): p. 863-7.

299. Reichardt, V. L., et al., *Idiotype vaccination using dendritic cells after autologous peripheral blood stem cell transplantation for multiple myeloma—a feasibility study*. Blood, 1999. 93(7): p. 2411-9.

300. Lim, S. H. and R. Bailey-Wood, *Idiotypic protein-pulsed dendritic cell vaccination in multiple myeloma*. Int J Cancer, 1999. 83(2): p. 215-22.

301. Motta, M. R., et al., *Generation of dendritic cells from CD14+ monocytes positively selected by immunomagnetic adsorption for multiple myeloma patients enrolled in a clinical trial of anti-idiotype vaccination*. Br J Haematol, 2003. 121(2): p. 240-50.

302. Reichardt, V. L., et al., *Idiotype vaccination of multiple myeloma patients using monocyte-derived dendritic cells*. Haematologica, 2003. 88(10): p. 1139-49.

303. Guardino, A. E., et al., *Production of myeloid dendritic cells (DC) pulsed with tumor-specific idiotype protein for vaccination of patients with multiple myeloma*. Cytotherapy, 2006. 8(3): p. 277-89.

304. Lacy, M. Q., et al., *Idiotype-pulsed antigen-presenting cells following autologous transplantation for multiple myeloma may be associated with prolonged survival*. Am J Hematol, 2009. 84(12): p. 799-802.

305. Yi, Q., et al., *Optimizing dendritic cell-based immunotherapy in multiple myeloma: intranodal injections of idiotype-pulsed CD40 ligand-matured vaccines led to induction of type-1 and cytotoxic T-cell immune responses in patients*. Br J Haematol, 2010. 150(5): p. 554-64.

306. Rollig, C., et al., *Induction of cellular immune responses in patients with stage-I multiple myeloma after vaccination with autologous idiotype-pulsed dendritic cells*. J Immunother, 2011. 34(1): p. 100-6.

307. Zahradova, L., et al., *Efficacy and safety of Id-protein-loaded dendritic cell vaccine in patients with multiple myeloma—phase II study results*. Neoplasma, 2012. 59(4): p. 440-9.

308. Timmerman, J. M., et al., *Idiotype-pulsed dendritic cell vaccination for B-cell lymphoma: clinical and immune responses in 35 patients*. Blood, 2002. 99(5): p. 1517-26.

309. Maier, T., et al., *Vaccination of patients with cutaneous T-cell lymphoma using intranodal injection of autologous tumor-lysate-pulsed dendritic cells*. Blood, 2003. 102(7): p. 2338-44.

310. Di Nicola, M., et al., *Vaccination with autologous tumor-loaded dendritic cells induces clinical and immunologic responses in indolent B-cell lymphoma patients with relapsed and measurable disease: a pilot study*. Blood, 2009. 113(1): p. 18-27.

311. Hus, I., et al., *Allogeneic dendritic cells pulsed with tumor lysates or apoptotic bodies as immunotherapy for patients with early-stage B-cell chronic lymphocytic leukemia*. Leukemia, 2005. 19(9): p. 1621-7.

312. Li, L., et al., *Immunotherapy for patients with acute myeloid leukemia using autologous dendritic cells generated from leukemic blasts*. Int J Oncol, 2006. 28(4): p. 855-61.

313. Roddie, H., et al., *Phase I/II study of vaccination with dendritic-like leukaemia cells for the immunotherapy of acute myeloid leukaemia*. Br J Haematol, 2006. 133(2): p. 152-7.

314. Litzow, M. R., et al., *Testing the safety of clinical-grade mature autologous myeloid DC in a phase I clinical immunotherapy trial of CML*. Cytotherapy, 2006. 8(3): p. 290-8.

315. Westermann, J., et al., *Vaccination with autologous non-irradiated dendritic cells in patients with bcr/abl+ chronic myeloid leukaemia*. Br J Haematol, 2007. 137(4): p. 297-306.

316. Hus, I., et al., *Vaccination of B-CLL patients with autologous dendritic cells can change the frequency of leukemia antigen-specific CD8+ T cells as well as CD4+ CD25+FoxP3+ regulatory T cells toward an antileukemia response*. Leukemia, 2008. 22(5): p. 1007-17.

317. Palma, M., et al., *Development of a dendritic cell-based vaccine for chronic lymphocytic leukemia*. Cancer Immunol Immunother, 2008. 57(11): p. 1705-10.

318. Van Tendeloo, V. F., et al., *Induction of complete and molecular remissions in acute myeloid leukemia by Wilms' tumor 1 antigen-targeted dendritic cell vaccination*. Proc Natl Acad Sci USA, 2010. 107(31): p. 13824-9.

319. Iwashita, Y., et al., *A phase I study of autologous dendritic cell-based immunotherapy for patients with unresectable primary liver cancer*. Cancer Immunol Immunother, 2003. 52(3): p. 155-61.

320. Lee, W. C., et al., *Vaccination of advanced hepatocellular carcinoma patients with tumor lysate-pulsed dendritic cells: a clinical trial*. J Immunother, 2005. 28(5): p. 496-504.

321. Butterfield, L. H., et al., *A phase I/II trial testing immunization of hepatocellular carcinoma patients with dendritic cells pulsed with four alpha-fetoprotein peptides*. Clin Cancer Res, 2006. 12(9): p. 2817-25.

322. Palmer, D. H., et al., *A phase II study of adoptive immunotherapy using dendritic cells pulsed with tumor lysate in patients with hepatocellular carcinoma*. Hepatology, 2009. 49(1): p. 124-32.

323. El Ansary, M., et al., *Immunotherapy by autologous dendritic cell vaccine in patients with advanced HCC*. J Cancer Res Clin Oncol, 2013. 139(1): p. 39-48.

324. Tada, F., et al., *Phase I/II study of immunotherapy using tumor antigen-pulsed dendritic cells in patients with hepatocellular carcinoma*. Int J Oncol, 2012. 41(5): p. 1601-9.

325. Ueda, Y., et al., *iDendritic cell-based immunotherapy of cancer with carcinoembryonic antigen-derived, HLA-A24-restricted CTL epitope: Clinical outcomes of 18 patients with metastatic gastrointestinal or lung adenocarcinomas*. Int J Oncol, 2004. 24(4): p. 909-17.

326. Hirschowitz, E. A., et al., *Autologous dendritic cell vaccines for non-small-cell lung cancer*. J Clin Oncol, 2004. 22(14): p. 2808-15.

327. Chang, G. C., et al., *A pilot clinical trial of vaccination with dendritic cells pulsed with autologous tumor cells derived from malignant pleural effusion in patients with late-stage lung carcinoma*. Cancer, 2005. 103(4): p. 763-71.

328. Yannelli, J. R., et al., *The large scale generation of dendritic cells for the immunization of patients with non-small cell lung cancer (NSCLC)*. Lung Cancer, 2005. 47(3): p. 337-50.

329. Ishikawa, A., et al., *A phase I study of alpha-galactosylceramide (KRN7000)-pulsed dendritic cells in patients with advanced and recurrent non-small cell lung cancer*. Clin Cancer Res, 2005. 11(5): p. 1910-7.

330. Antonia, S. J., et al., *Combination of p53 cancer vaccine with chemotherapy in patients with extensive stage small cell lung cancer*. Clin Cancer Res, 2006. 12(3 Pt 1): p. 878-87.

331. Perrot, I., et al., *Dendritic cells infiltrating human non-small cell lung cancer are blocked at immature stage*. J Immunol, 2007. 178(5): p. 2763-9.

332. Hirschowitz, E. A., et al., *Immunization of NSCLC patients with antigen-pulsed immature autologous dendritic cells*. Lung Cancer, 2007. 57(3): p. 365-72.

333. Baratelli, F., et al., *Pre-clinical characterization of GMP grade CCL21-gene modified dendritic cells for application in a phase I trial in non-small cell lung cancer*. J Transl Med, 2008. 6: p. 38.

334. Hegmans, J. P., et al., *Consolidative dendritic cell-based immunotherapy elicits cytotoxicity against malignant mesothelioma*. Am J Respir Crit Care Med, 2010. 181(12): p. 1383-90.

335. Um, S. J., et al., *Phase I study of autologous dendritic cell tumor vaccine in patients with non-small cell lung cancer*. Lung Cancer, 2010. 70(2): p. 188-94.

336. Chiappori, A. A., et al., *INGN-225: a dendritic cell-based p53 vaccine (Ad.p53-DC) in small cell lung cancer: observed association between immune response and enhanced chemotherapy effect*. Expert Opin Biol Ther, 2010. 10(6): p. 983-91.

337. Perroud, M. W., Jr., et al., *Mature autologous dendritic cell vaccines in advanced non-small cell lung cancer: a phase I pilot study*. J Exp Clin Cancer Res, 2011. 30: p. 65.

338. Skachkova, O. V., et al., *Immunological markers of anti-tumor dendritic cells vaccine efficiency in patients with non-small cell lung cancer*. Exp Oncol, 2013. 35(2): p. 109-13.

339. Hernando, J. J., et al., *Vaccination with autologous tumour antigen pulsed dendritic cells in advanced gynaecological malignancies: clinical and immunological evaluation of a phase I trial*. Cancer Immunol Immunother, 2002. 51(1): p. 45-52.

340. Rahma, O. E., et al., *A gynecologic oncology group phase II trial of two p53 peptide vaccine approaches: subcutaneous injection and intravenous pulsed dendritic cells in high recurrence risk ovarian cancer patients*. Cancer Immunol Immunother, 2012. 61(3): p. 373-84.

341. Chu, C. S., et al., *Phase I/II randomized trial of dendritic cell vaccination with or without cyclophosphamide for consolidation therapy of advanced ovarian cancer in first or second remission*. Cancer Immunol Immunother, 2012. 61(5): p. 629-41.

342. Kandalaft, L. E., et al., *A Phase I vaccine trial using dendritic cells pulsed with autologous oxidized lysate for recurrent ovarian cancer*. J Transl Med, 2013. 11: p. 149.

343. Lepisto, A. J., et al., *A phase I/II study of a MUC1 peptide pulsed autologous dendritic cell vaccine as adjuvant therapy in patients with resected pancreatic and biliary tumors*. Cancer Ther, 2008. 6(B): p. 955-964.

344. Rong, Y., et al., *A phase I pilot trial of MUC1-peptide-pulsed dendritic cells in the treatment of advanced pancreatic cancer*. Clin Exp Med, 2012. 12(3): p. 173-80.

345. Endo, H., et al., *Phase I trial of preoperative intratumoral injection of immature dendritic cells and OK-432 for resectable pancreatic cancer patients*. J Hepatobiliary Pancreat Sci, 2012. 19(4): p. 465-75.

The invention claimed is:

1. A method of treating or ameliorating the effects of type 1 diabetes comprising the steps of: a) identifying a patient diagnosed with type 1 diabetes b) withdrawing from said patient a population of peripheral blood monocyte cells; c) contacting said peripheral blood monocyte cells with a mesenchymal stem cell population derived from umbilical cord tissue and/or conditioned media generated from said mesenchymal stem cell population derived from umbilical cord; d) pulsing said peripheral blood monocyte cells with one or more antigens associated with diabetes; e) extracting exosomes from said peripheral blood monocyte cells; and f) administering said exosomes into the patient diagnosed with type 1 diabetes.

2. The method of claim 1, wherein said mesenchymal stem cell population derived from umbilical cord tissue lack expression of the markers: a) CD14; b) CD45; and c) CD34.

3. The method of claim 2, wherein said mesenchymal stem cell population derived from umbilical cord tissue does not express the following markers: a) CD117; b) CD31; c) CD34; and d) CD45.

4. The method of claim 3, wherein said mesenchymal stem cell population derived from umbilical cord tissue express, relative to a human fibroblast, increased levels of interleukin 8 and reticulon 1.

5. The method of claim 3, wherein said mesenchymal stem cell population derived from umbilical cord tissue has the potential to differentiate into cells of at least a skeletal muscle, vascular smooth muscle, pericyte or vascular endothelium phenotype.

6. The method of claim 3, wherein said umbilical cord tissue derived mesenchymal stem cell population maintains a normal karyotype upon passaging.

7. The method of claim 1, wherein said umbilical cord tissue-derived mesenchymal stem cell population is positive for alkaline phosphatase staining.

8. The method of claim 1, wherein said exosomes express CD9.

* * * * *